US008138327B2

(12) United States Patent
Unwalla et al.

(10) Patent No.: US 8,138,327 B2
(45) Date of Patent: Mar. 20, 2012

(54) INDUCIBLE SYSTEMS AND METHODS FOR CONTROLLING SIRNA EXPRESSION

(75) Inventors: Hoshang Unwalla, Monrovia, CA (US); John J. Rossi, Alta Loma, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 11/283,410

(22) Filed: Nov. 21, 2005

(65) Prior Publication Data

US 2006/0122139 A1 Jun. 8, 2006

Related U.S. Application Data

(60) Provisional application No. 60/629,890, filed on Nov. 23, 2004.

(51) Int. Cl.
*C07H 21/04* (2006.01)
*C12N 15/11* (2006.01)
*C12N 5/00* (2006.01)
*C12Q 1/68* (2006.01)
*C12N 15/09* (2006.01)

(52) U.S. Cl. ....... 536/24.5; 514/44 A; 435/6.1; 435/325; 435/375; 435/455

(58) Field of Classification Search .................. 435/4, 6, 435/366; 514/44; 536/23.1, 24.5; 424/93.2
See application file for complete search history.

(56) References Cited

U.S. PATENT DOCUMENTS

| | | | |
|---|---|---|---|
| 2002/0160393 A1* | 10/2002 | Symonds et al. .................. 435/6 |
| 2003/0170891 A1* | 9/2003 | McSwiggen .................. 435/366 |
| 2004/0002077 A1* | 1/2004 | Taira et al. .......... 435/6 |
| 2004/0091918 A1* | 5/2004 | Rossi et al. ...... 435/6 |
| 2004/0198967 A1* | 10/2004 | Allen et al. ......... 536/23.1 |
| 2005/0008617 A1* | 1/2005 | Chen et al. .......... 424/93.2 |

FOREIGN PATENT DOCUMENTS

WO    WO 03022052 A1 *   3/2003

OTHER PUBLICATIONS

Hosono et al., Adenovirus vector-mediated doxycycline-inducible RNA interference, Aug. 2004, Human Gene Therapy, vol. 15, pp. 813-819.*
Lin et al., Development of a tightly regulated U6 promoter for shRNA expression, 2004, FEBS Letters, vol. 577, pp. 376-380.*
Malphettes et al., Macrolide- and Tetracycline-adjustable siRNA-mediated gene silencing in mammalian cells using polymerase II-dependent promoter derivatives, 2004, Biotechnology and Bioengineering, vol. 88, pp. 417-425.*
Miyagishi et al., Optimization of an siRNA-expression system with an improved hairpin and its significant suppressive effects in mammalian cells, 2004, The Journal of Gene Medicine, vol. 6, pp. 715-723.*
Fraisier et al., High level inhibition of HIV replication with combination RNA decoys expressed from an HIV-Tat inducible vector, 1998, Gene Therapy, vol. 5, pp. 1665-1676.*
Mavankal et al., Human immunodeficiency virus type 1 and type 2 Tat proteins specifically interact with RNA polymerase II, 1996, PNAS, vol. 93, pp. 2089-2094.*
Lam et al., Inducible expression of double-stranded RNA directs specific genetic interference in *Drosophila*, 2000, Current Biology, vol. 10, pp. 957-963.*
Taira et al., Cell cycle-dependent switch of up- and down-regulation of human hsp70 gene expression by interaction between c-myc and CBF/NF-Y, 1999, The Journal of Biological Chemistry, vol. 274, pp. 24270-24279.*
Pagans et al., The *Drosophila* transcription factor tramtrack (TTK) interacts with Trithorax-like (GAGA) and represses GAGA-mediated activation, 2002, Nucleic Acids Research, vol. 30, pp. 4406-4413.*
Verhoef et al., Optimal Tat-mediated activation of the HIV-1 LTR promoter requires a full-length TAR RNA hairpin, 1997, Nucleic Acids Research, vol. 25, pp. 496-502.*
Tang et al., Promoter-proxminal pausing on the hsp70 promoter in *Drosophila* melanogaster depends on the upstream regulator, 2000, Molecular and Cellular Biology, vol. 20, pp. 2569-2580.*
Sirven et al., The human immunodeficiency virus type-1 central DNA flap is a crucial determinant for lentiviral vector nuclear import and gene transduction of human hematopoietic stem cells, 2000, Blood, vol. 96, pp. 4103-4110.*
Ramezani et al., Lentiviral vectors for enhanced gene expression in human hematopoietic cells, 2000, Molecular Therapy, vol. 2, pp. 458-469.*
An, D.S., "Efficient Lentiviral Vectors for Short Hairpin RNA Delivery into Human Cells", Human Gene Therapy, vol. 14, Aug. 10, 2003, pp. 1207-1212.
Bridge, A.J., et al. "Induction of an interferon response by RNAi vectors in mammalian cells", Nature Genetics, vol. 34, No. 3, Jul. 2003, pp. 263-264.
Brummelkamp, T.R.., et al., "A System for Stable Expression of Short Interfering RNASs in Mammalian Cells", Science, vol. 296, Apr. 19, 2002, pp. 550-553.
Caplen, N. J., et al., "Specific inhibition of gene expression by small double-stranded RNAs in invertebrate and vertebrate systems", PNAS, vol. 98, No. 17, Aug. 14, 2001, pp. 9742-9747.
Elbashir, S.M., "Duplexes of 21-nucleotide RNAs mediated RNA interference in cultured mammalian cells", Nature, vol. 411, May 24, 2001, pp. 494-498.

(Continued)

*Primary Examiner* — Dana Shin
(74) *Attorney, Agent, or Firm* — Rothwell, Figg, Ernst & Manbeck P.C.

(57) ABSTRACT

An inducible system and methods for controlling expression of siRNA are provided. An inducible system for producing siRNA only in the presence of HIV TAT, and methods for inhibiting HIV-1 gene expression in cells comprising such inducible system also are provided.

30 Claims, 15 Drawing Sheets

OTHER PUBLICATIONS

Fire, et al, "Potent and Specific genetic interference by double-stranded RNA in *Caenorhabditis elegans*", Nature, vol. 391, Feb. 19, 1998, pp. 806-811.

Grishok, A., et al., "Genes and Mechanisms Related to RNA Interference Regulate Expression of the Small Temporal RNAs that Control *C. elegans* Developmental Timing", Cell, vol. 106, Jul. 13, 2001, pp. 23-34.

Han, et al., "Transactivation of heterologous promoters by HIV-1 tat", Nucleic Acids Research, vol. 19, No. 25, 1991, pp. 7225-7229.

Hutvágner, G., et al., "A Cellular Function for the RNA-Interference Enzyme Dicer in the Maturation of the let-7 Small Temporal RNA", Science, vol. 293, Aug. 3, 2001, pp. 834-838.

Kennerdell, J.R., et al., "Use of dsRNA-Mediated Genetic Interference to Demonstrate that *frizzled* and *frizzled 2* Act in the Wingless Pathway", Cell, vol. 95, Dec. 23, 1998, pp. 1017-1026.

Lee, N. S., et al., "Expression of small interfering RNAs targeted against HIV-1 *rev* transcripts in human cells", Nature Biotechnology, vol. 19, May 2002, pp. 500-505.

Lipardi, C., et al., "RNAi as Random Degradative PCR: siRNA Primers Convert mRNA into dsRNAs that are Degraded to Generate New siRNAs", Cell, vol. 107, Nov. 2, 2001, pp. 297-307.

Matsukura, S., et al., "Establishment of conditional vectors for hairpin siRNA knockdowns", Nucleic Acids Research, vol. 31, No. 15, 2003, 5 pages.

Miyagishi, M., et al., "U6 promoter-driven siRNAs with four uridine 3' overhangs efficiently suppress targeted gene expression in mammalian cells", Nature Biotechnology, vol. 19, May 2002, pp. 497-500.

Moss, E.G., et al., "Small-interfering RNAs in the radar of the interferon system", Nature Cell Biology, vol. 5, No. 9, Sep. 2003, pp. 771-772.

Sijen, T., et al., "On the Role of RNA Amplification in dsRNA-Triggered Gene Silencing", Cell, vol. 107, Nov. 16, 2001, pp. 465-476.

Sledz, C.A., et al., "Activation of the interferon system by short-interfering RNAs", Nature Cell Biology, vol. 5, No. 9, Sep. 2003, pp. 834-839.

Southgate, C.D., "The HIV-1 Tat protein activates transcription from an upstream DNA-binding site: implications for Tat function", Genes & Development, vol. 5, 1991, pp. 2496-2507.

Unwalla, H.J., et al., "Negative feedback inhibition of HIV-1 by Tat-inducible expression of siRNA," Nature Biotechnology, vol. 22, No. 12, Dec. 2004, pp. 1573-1578 plus Supplementary Figures 1 and 2.

van de Wetering, M., et al., "Specific inhibition of gene expression using a stably integrated, inducible small-interfering-RNA vector", EMBO reports, vol. 4, No. 6, 2003, pp. 609-615.

Wianny, F., et al., "Specific interference with gene function by double-stranded RNA in early mouse development", Nature Cell Biology, vol. 2, Feb. 2000, pp. 70-75.

Wiznerowicz, M., et al., "Conditional Suppression of Cellular Genes: Lentivirus Vector-Mediated Drug-Inducible RNA Interference", Journal of Virology, vol. 77, No. 16, Aug. 2003, pp. 8957-8961.

Xia, H., et al., "siRNA-mediated gene silencing in vitro and in vivo", Nature Biotechnology, vol. 20, Oct. 2002, pp. 1006-1010.

Yi, R., et al., "Exportin-5 mediates the nuclear export of pre-microRNAs and short hairpin RNAs", Genes & Development, vol. 17, 2003, pp. 3011-3016.

* cited by examiner

A shRNA sequence pIND expression cassette pIND-shRNAmpolyA mpIND-shRNAmpolyA

B pIND-RevEGFP mpIND-shRNApolyA pIND-shRNApolyA

Irrelevent siRNA

D

A

B

SEQUENCE LISTING

```
<160> NUMBER OF SEQ ID NOS: 3

<210> SEQ ID NO 1
<211> LENGTH: 65
<212> TYPE: RNA
<213> ORGANISM: Artificial
<220> FEATURE:
<223> OTHER INFORMATION: short hairpin RNA

<400> SEQUENCE: 1
gccugugccu cuucaguuac cgcuugaguu caagagacuc aagcgguagc ugaagaggca      60
caggc                                                                 65

<210> SEQ ID NO 2
<211> LENGTH: 90
<212> TYPE: DNA
<213> ORGANISM: Artificial
<220> FEATURE:
<223> OTHER INFORMATION: PCR primer

<400> SEQUENCE: 2
gcctgtgcct cttcagttac cgcttgagtt caagagactc aagcggtagc tgaagaggca      60
caggcttcta gaactagtaa taaaggatcc                                      90

<210> SEQ ID NO 3
<211> LENGTH: 82
<212> TYPE: DNA
<213> ORGANISM: Artificial
<220> FEATURE:
<223> OTHER INFORMATION: PCR Primer

<400> SEQUENCE: 3
cggtctagac gcggccgcac acaaaaaacc aacacacgga tccaatgaaa ataaaggatc      60
ctttattact agttctagaa gc                                              82
```

INDUCIBLE SYSTEMS AND METHODS FOR CONTROLLING SIRNA EXPRESSION

CROSS-REFERENCE TO RELATED APPLICATION

The present application is related to and claims priority under 35 U.S.C. §119(e) to U.S. provisional patent application Ser. No. 60/629,890 filed 23 Nov. 2004, incorporated herein by reference.

STATEMENT REGARDING FEDERALLY SPONSORED RESEARCH

The present invention was made in part with Government support under Grant Numbers AI29329, AI42552 and HL074704 awarded by the National Institutes of Health. The Government may have certain rights in this invention.

FIELD OF THE INVENTION

The present invention relates to RNA interference. In particular, the invention relates to an inducible system and methods for controlling the expression of siRNA and to use of the system for inhibiting gene expression.

BACKGROUND OF THE INVENTION

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The proteins mediating RNA interference (RNAi) are part of an evolutionarily conserved cellular pathway that processes endogenous cellular RNAs to silence developmentally important genes (Grishok et al., 2001; Hutvagner et al., 2001). RNAi is a potent inhibitor of targeted gene expression in a wide variety of organisms (Wianny and Zernica-Goetz, 2000; Kennerdell and Carthew, 1998; Fire et al., 1998). The triggers for RNAi are small interfering RNAs (siRNAs) that are processed from long double stranded or hairpin RNA precursors and become part of a ribonucleoprotein complex (Lipardi et al., 2001; Sijen et al., 2001). RNAi mediated gene silencing in mammalian cells has been achieved by either transfecting synthetic dsRNA (Caplan et al., 2001; Elbashir et al., 2001), plasmids (Brummelkamp et al., 2002; Lee et al., 2002; Miyagishi and Taira, 2002) expressing siRNA as individual sense and antisense strands, or the use of short hairpin RNAs (shRNAs) 21-29 nucleotides long which are processed by the RNAse III family member Dicer to siRNA sized molecules that guide the cleavage of cognate mRNA (Xia et al., 2002; An et al., 2003). Most expression systems produce shRNAs from Pol III promoters which provide discrete 5' and 3' termini that are further processed into siRNAs. These transcripts mimic micro RNA precursors in structure and are most probably cytoplasmically exported by the transport factor exporting 5 (Ye et al., 2003).

Early on it was demonstrated that a Pol II promoter could also be used to express shRNAs (Xia et al., 2002). Some of the restrictions for expression of a functional shRNA include elimination of non-base paired 5' sequences and the use of a minimal poly A signal (Xia et al., 2002). There are several potential advantages to utilizing Pol II expressed shRNAs including tissue specific promoters and inducible transcription. Given the requirement for a poly A signal at the 3' end of the transcriptional units, it is not known how the final shRNAs are produced, and which transport system is used to export these to the cytoplasm. Nevertheless, it is clear that functional siRNAs can be produced by Pol II systems.

Small interfering RNAs (siRNAs) can induce potent gene silencing by directing degradation of cognate mRNAs. Controlled expression of siRNA may be important in clinical settings because it has been reported that some siRNA and shRNA sequences can induce a non-specific interferon response. The present invention thus provides controlled expression of siRNA.

SUMMARY OF THE INVENTION

The present invention relates to an inducible system for controlling expression of siRNA, including short hairpin RNA (shRNA). The inducible system comprises a suitable promoter operatively associated with an inducible element. siRNA is preferably produced only in the presence of an inducer which is specific for the inducible element. The invention is useful for inhibiting gene expression.

In one aspect, the present invention provides an inducible fusion promoter for expressing siRNA or shRNA. The inducible fusion promoter comprises a suitable promoter operatively associated with an inducible element. In one embodiment, the inducible element is responsive to a tissue specific, viral specific, cellular specific or engineered transcription factor. In another embodiment, the inducible element is responsive to a viral specific transcription factor. In a further embodiment, the virus is HIV. In one embodiment, the inducer is TAT. In another embodiment the inducible element is the HIV-1 LTR containing the TAR sequences.

In a second aspect, the present invention provides for the inducible expression of siRNA (shRNA) in response to an inducer through the use of the inducible fusion promoter to which the siRNA (shRNA) is operably linked. The fusion promoter should express siRNA (shRNA) only in cells that express the inducer. In one embodiment, the cells naturally express the inducer. In another embodiment, the cells are viral infected cells that express the inducer. In a further embodiment, the cells are cells transfected with a vector that expresses the inducer. In one embodiment, the cells are cells harboring HIV-1. In a second embodiment, the cells are cells transfected with a vector expressing the TAT gene.

In a third aspect, the present invention provides pharmaceutical compositions containing the inducible siRNA (shRNA).

In a fourth aspect, the present invention provides methods for selectively reducing the expression of a gene product from a desired target gene in a cell, as well as for treating diseases caused by the expression of the gene. In one embodiment, the method involves introducing into the environment of a cell an amount of a inducible siRNA (shRNA) such that a sufficient portion of the siRNA (shRNA) can be induced in the cell to cause a reduction in the expression of the target gene.

siRNA expression according to the present invention translates to an efficient inhibition of gene expression in a transient as well as in a stable long-term setting. These results demonstrate for the first time a functional inducible system for siRNAs which are useful, for example, for siRNA based gene therapy. The present invention is particularly advantageous in that it addresses the safety concerns of off-target effects sometimes or often associated with expression of shRNA. These advantages thus enhance the utility of the present invention in the clinical setting.

BRIEF DESCRIPTION OF THE FIGURES

In FIG. 5A, the results of a Northern blot analysis are shown in which total RNA is extracted from 293 cells co-transfected with shRNA constructs and pNL4-3. A strong 39 base partially processed form can be observed when the blot was probed to detect the antisense strand. This product was observed when the blot was probed to detect the antisense strand. This product was not detectable when a probe complementary to the sense strand was used. The upper band is the partially processed shRNA and the lower band is the fully processed siRNA. FIG. 5B is a schematic depiction of shRNA processing. An shRNA that is processed fully from the 3' end should result in three molecular species, a partially processed hairpin with the loop processed at the 5' end of the antisense strand, a fully processed loop and a partially processed species with the loop processed at the 3' end of the sense strand of size ca 39 bases.

DETAILED DESCRIPTION OF THE INVENTION

Figure 1A:
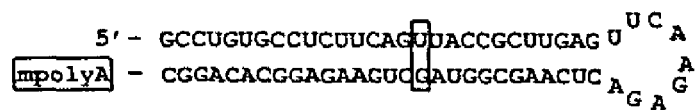
FIG. 1A shows an shRNA sequence and expression cassettes. In particular, an shRNA sequence (SEQ ID NO:1) with minimal polyadenylation signal sequence is shown. One of the boxes shows the position of the G-U wobble pairing. Also shown is a schematic representation of the pIND expression cassette from the pIND vector (Invitrogen) and shRNA expression cassette with and without the 5' leader element of the minimal hsp70 promoter from the pIND vector. B=Bgl II site; X=Xma I site; TS=Transcription start; MCS=Multiple cloning site; LE=Leader element; S=Sense strand; AS=Antisense strand; L=Loop.
Figure 1A:
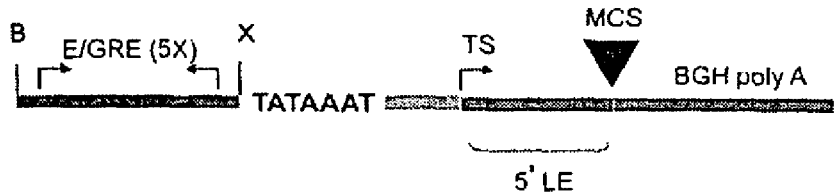
Figure 1A:
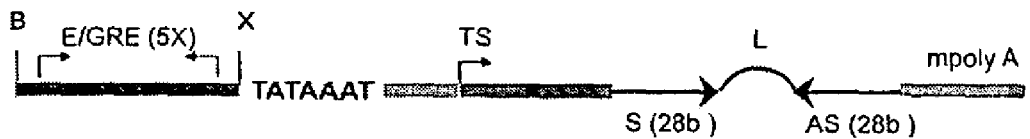
Figure 1A:
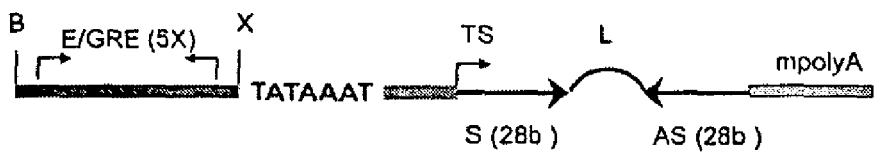

The present invention relates to an inducible system for controlling expression of siRNA, including short hairpin RNA (shRNA). The inducible system comprises a nucleic acid construct that comprises a suitable promoter operatively associated with an inducible element. The nucleic acid construct may also further comprise siRNA (shRNA) operably associated with the promoter. The siRNA is preferably produced only in the presence of an inducer which is specific for the inducible element. The invention is useful for inhibiting gene expression.

As used herein, "nucleic acid construct" or "construct" refers to an isolated polynucleotide which is introduced into a host cell. This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

In one aspect, the present invention provides an inducible fusion promoter for expressing siRNA or shRNA. The inducible fusion promoter is a nucleic acid construct that comprises a suitable promoter operatively associated with an inducible element in one embodiment, the inducible element is responsive to an inducer. In another embodiment, the inducer is a tissue specific transcription factor, a viral specific transcription factor, a cellular specific transcription factor or an engineered transcription factor. In further embodiment, the inducible element is responsive to a viral specific transcription factor. In a still further embodiment, the virus is HIV. In one embodiment, the inducer is TAT. In another embodiment the inducible element is the HIV-1 LTR containing the TAR sequences.

As used herein "operably linked" or "operably associated" includes reference to a functional linkage of at least two sequences. For example, operably linked includes linkage between a promoter and a second sequence, wherein the promoter sequence initiates and mediates transcription of the DNA sequence corresponding to the second sequence. Operably associated includes linkage between an inducing element and a promoter, wherein the inducing element acts as a transcriptional activator of the promoter.

As used herein, "promoter" includes reference to a region of DNA that is involved in recognition and binding of an RNA polymerase and other proteins to initiate transcription. In one embodiment, the promoter is a Pol II promoter. Any Pol II promoter may be used in accordance with the present invention. In one embodiment, the Pol II promoter is a heat shock promoter. In another embodiment, the heat shock promoter is a minimal heat shock promoter. In a further embodiment, the minimal heat shock promoter is the *Drosophila* hsp70 minimal heat shock promoter.

As used herein, an "inducible element" includes an element that confers regulation on transcription of a downstream expressed region under inducing conditions. It may be obtained from enhancer regions that are also inducible. Removal of an inducible element from the downstream expressed region would be expected to decrease expression of a downstream region under inducing conditions. Inducible elements (e.g., consensus sequences known in the art) are usually between about 4 and 100 nucleotides in length.

In one embodiment, the inducible element is HIV-1 TAR (transactivation-responsive region). TAR resides within the R region of the HIV-1 long terminal repeat (LTR), between −17 and +54 with respect to the initiation site of viral transcription (Feng and Holland, 1988; Rosen et al., 1985; Muesing et al., 1987). The RNA encoded between +1 and +59 has the potential to from an extensive stem-loop secondary structure which, as a portion of the untranslated leader RNA, would be common to all HIV-1 mRNAs (Muesing et al., 1987; Okamoto and Wong-Staal, 1986). Studies have shown that the sequence $^{+30}$CUGGG$^{+34}$ in TAR within the loop of the hairpin structure is required for TAT transactivation (Feng and Holland, 1988).

As used herein, "encodes" or "encoding" refers to a DNA sequence which can be processed to generate an RNA and/or polypeptide.

As used herein, "inducer" includes an agent that induces, especially a substance that is capable of activating transcription from specific genes within a cell.

In one embodiment, the inducer is HIV-1 TAT (trans-activator of transcription). HIV-1 TAT is a 14 kDa viral protein involved in the regulation of HIV-1 transcriptional elongation (Kao et al., 1987; Feinberg et al., 1991; Marciniak and Sharp, 1991) and in its presence, viral replication increases by greater than 100-fold (Cullen, 1986; Muesing et al., 1987). It functions to trigger efficient RNA chain elongation by binding to TAR RNA, which forms the initial portion of the HIV-1 transcript (Berkhout et al., 1989). The interaction between TAT and TAR is critical for virus replication and mutations in TAT that alter the RNA-binding site result in defective viruses. Furthermore, virus replication can be strongly inhibited by the overexpression of TAR RNA sequences that act as competitive inhibitors of regulatory protein binding (Graham and Maio, 1990).

In a preferred embodiment, the present invention relates to an HIV inducible shRNA system, preferably containing a suitable promoter operably associated with an inducible element that is inducible by HIV TAT. In one embodiment, part of a TATA box region, such as the *Drosophila* hsp70 TATA box region, is cloned downstream of the HIV-1 LTR containing the TAR region.

In one embodiment of the invention, an anti-HIV shRNA expressed from a Pol II promoter was demonstrated to inhibit HIV-1 gene expression in mammalian cells. This preferred strategy was applied to design a novel promoter system where, in a preferred embodiment, the HIV-1 LTR is fused to the *Drosophila* hsp70 minimal heat shock promoter. This system is inducible by HIV-1 TAT, providing regulated expression of the shRNA.

In another aspect of the invention, an inducible system comprises a suitable promoter operatively associated with an HIV TAR region, which instead of acting as a transcriptional activator by recruiting TAT, acts as a repressor by recruiting, for example, N-TEF, thereby suppressing transcription from the promoter. siRNA (shRNA) expression then can be induced in response to inducing elements (e.g., transcription factors) associating with inducible elements (e.g., regulatory elements), which also can be operatively associated with the promoter.

In still another aspect of the invention, a nucleic acid construct is provided to encode the siRNA (shRNA) for any specific target sequence. Any siRNA (shRNA) can be inserted into the construct containing the inducible system, such that the encoded siRNA (shRNA) selectively targets and suppresses the target sequence.

A cell containing a nucleic acid construct of the present invention is also provided. By "host cell" is meant a cell which contains an introduced nucleic acid construct and supports the replication and/or expression of the construct. In one embodiment, the cell is a cell that naturally contains the inducer. In another embodiment, the cell is one that is infected by HIV-1, and thus produces TAT. In one embodiment, cells infected with HIV-1 can efficiently induce siRNA (shRNA) expression from a construct according to the present invention. In a further embodiment, the cell is one that is transfected with a nucleic acid construct comprising a TAT coding sequence operably linked to a promoter, such that TAT is produced in the cell. The promoter associated with the TAT encoding nucleic acid sequence may be any promoter, such as a constitutive promoter, a tissue-preferred promoter, an inducible promoter or a derepressible promoter.

The term "introducing" encompasses a variety of methods of introducing DNA into a cell, either in vitro or in vivo, such methods including transformation, transduction, transfection, and infection. Vectors are useful and preferred agents for introducing DNA encoding the interfering RNA molecules into cells. Possible vectors include plasmid vectors and viral vectors. Viral vectors include retroviral vectors, lentiviral vectors, or other vectors such as adenoviral vectors or adeno-associated vectors.

In a further aspect of the invention, a method for suppressing a target sequence is provided. The method employs the constructs above, in which a siRNA (shRNA) is designed to a region of the target sequence, and inserted into the construct. Upon introduction into a cell and upon induction of the inducible system, the siRNA (shRNA) produced suppresses expression of the targeted sequence. In one embodiment, the cell is one that is infected with HIV-1, and the invention provides a method of inhibiting viral replication, thus establishing a negative feedback loop. In another embodiment, the cell is one that is transfected with a nucleic acid construct comprising a nucleic acid sequence encoding TAT, and the invention provides a method of inhibiting any target sequence.

Transformation protocols as well as protocols for introducing nucleotide sequences into cells may vary depending on the type of cell targeted for transformation. Suitable methods of introducing the DNA construct into cells are well known in the art and include microinjection, electroporation, direct gene transfer, ballistic particle transformation, viral transformation, retroviral transformation and the like.

In some embodiments, transient expression may be desired. In those cases, standard transient transformation techniques may be used. Such methods include, but are not limited to viral transformation methods, and microinjection of DNA or RNA, as well other methods well known in the art.

Initial identification and selection of cells and/or plants comprising the DNA constructs may be facilitated by the use of marker genes. Gene targeting call be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Useful markers include positive and negative selectable markers as veil as markers that facilitate screening, such as visual markers.

Interfering RNA (RNAi) molecules, and more preferably siRNA molecules, produced and/or used in accordance with the invention include those types known in the art. The RNAi, and preferably siRNA, or shRNA, molecules are double-stranded (ds) RNAs, i.e., RNAs that contain a duplex region, that preferably contain about 19 to 23, or 21 to 29, base pairs, respectively. The molecules also preferably contain 3' overhangs, more preferably 3'UU or 3'TT overhangs. Each strand of the double stranded nucleic acid may comprise RNA, RNA analog(s) or RNA and DNA. Typically, the antisense strand of the siRNA is sufficiently complementary with the target sequence of the target gene. The siRNA and shRNA constructs are designed and prepared using techniques well known in the art, including those described in copending application Ser. No. 11/079,906 filed on 15 Mar. 2005, incorporated herein by reference. The siRNA or shRNA is operably associated with the inducible fusion promoter of the present invention.

The phrase "duplex region" refers to the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

As is known, RNAi methods are applicable to a wide variety of genes in a wide variety of organisms and the disclosed compositions and methods can be utilized in each of these contexts. Examples of genes which can be targeted by the disclosed compositions and methods include endogenous genes which are genes that are native to the cell or to genes that are not normally native to the cell. Without limitation these genes include oncogenes, cytokine genes, idiotype (Id) protein genes, prion genes, genes that expresses molecules that induce angiogenesis, genes for adhesion molecules, cell surface receptors, proteins involved in metastasis, proteases, apoptosis genes, cell cycle control genes, genes that express EGF and the EGF receptor, multi-drug resistance genes, such as the MDR1 gene.

As used herein, the phrases "target sequence" and "sequence of interest" are used interchangeably. Target sequence is used to mean the nucleic acid sequence that is selected for suppression of expression, and is not limited to polynucleotides encoding polypeptides. The target sequence comprises a sequence that is substantially or completely complementary to the miRNA. The target sequence can be RNA or DNA, and may also refer to a polynucleotide comprising the target sequence.

As used herein, "nucleic acid" means a polynucleotide and includes single or double-stranded polymer of deoxyribonucleotide or ribonucleotide bases. Nucleic acids may also include fragments and modified nucleotides.

As used herein, "vector" includes reference to a nucleic acid used in introduction of a polynucleotide of the invention into a host cell. Expression vectors permit transcription of a nucleic acid inserted therein.

More specifically, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSF, ETSI, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor-suppressor proteins (e.g., APC, BRCA1, BRCA2, MADH4, MCC, NF 1, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulnases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanlases, recombinases, reverse transcriptases, RUBISCOs, topoisomerases, and xylanases).

In one aspect, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Pathogens include RNA viruses such as flaviviruses, picornaviruses, rhabdoviruses, filoviruses, retroviruses, including lentiviruses, or DNA viruses Such as adenoviruses, poxviruses, herpes viruses, cytomegaloviruses, hepadnaviruses or others. Additional pathogens include bacteria, fungi, helminths, schistosomes and trypanosomes. Other kinds of pathogens can include mammalian transposable elements. Alternatively, the protein may be a tumor-associated protein or an autoimmune disease-associated protein.

The target gene may be derived from or contained in any organism. The organism may be a plant, animal, protozoa, bacterium, virus or fungus. See e.g., U.S. Pat. No. 6,506,559, incorporated herein by reference.

In another aspect, the present invention provides for a pharmaceutical composition comprising the dsRNA of the present invention. The dsRNA sample can be suitably formulated and introduced into the environment of the cell by any means that allows for a sufficient portion of the sample to enter the cell to induce gene silencing, if it is to occur. Many formulations for dsRNA are known in the art and can be used so long as dsRNA gains entry to the target cells so that it can act. See, e.g., U.S. published patent application Nos. 2004/0203145 A1 and 2005/0054598 A1, each incorporated herein by reference. For example, dsRNA can be formulated in buffer solutions such as phosphate buffered saline solutions, liposomes, micellar structures, and capsids. Formulations of dsRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing dsRNA into the environment of the cell will depend on the type of cell and the make up of its environment. For example, when the cells are found within a liquid, one preferable formulation is with a lipid formulation such as in lipofectamine and the dsRNA can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate dsRNA in a buffer or saline solution and directly inject the formulated dsRNA into cells, as in studies with oocytes. The direct injection of dsRNA duplexes may also be done. For suitable methods of introducing dsRNA see U.S. published patent application No. 2004/0203145 A1, incorporated herein by reference.

Suitable amounts of dsRNA must be introduced and these amounts can be empirically determined using standard methods. Typically, effective concentrations of individual dsRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

The method can be carried out by addition of the dsRNA compositions to any extracellular matrix in which cells can live provided that the dsRNA composition is formulated so that a sufficient amount of the dsRNA can enter the cell to exert its effect. For example, the method is amenable for use with cells present in a liquid such as a liquid culture or cell growth media, in tissue explants, or in whole organisms, including animals, such as mammals and especially humans.

The dsRNA can be formulated as a pharmaceutical composition which comprises a pharmacologically effective amount of a dsRNA and pharmaceutically acceptable carrier. A pharmacologically or therapeutically effective amount refers to that amount of a dsRNA effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general a suitable dosage unit of dsRNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the dsRNA can be administered once daily. However, the therapeutic agent may also be dosed in dosage units containing two, three, four, five, six or more sub-doses administered at appropriate intervals throughout the day. In that case, the dsRNA contained in each sub-dose must be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. In this embodiment, the dosage unit contains a corresponding multiple of the daily dose. Regardless of the formulation, the pharmaceutical composition must contain dsRNA in a quantity sufficient to inhibit expression of the target gene in the animal or human being treated. The composition can be compounded in Such a way that the sum of the multiple units of dsRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

In a further aspect, the present invention relates to a method for treating a subject having a disease or at risk of developing a disease caused by the expression of a target gene. In this embodiment, the dsRNA can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoictic origin, e.g., arising from myeloid, lymphoid or erythroid lineages, or precursor cells thereof.

The present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyclitis, acute necrotizinig hemorrhagic encephalopathy, idiopathic bilateral progressive sensorineural hearing, loss, aplastic anemia, pure red cell anemia, idiopathic thrombocytopenia, polychonidritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-lost disease, cases of transplantation, and allergy.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

The dsRNA of the present invention can also be used to inhibit the expression of the multi-drug resistance 1 gene ("MDR1"). "Multi-drug resistance" (MDR) broadly refer-s to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs and Ling, 1994). Moreover, expression of Pgp has been linked to the development of MDR in human cancer, particularly in the leukemias, lymphomas, multiple myeloma, neuroblastoma, and soft tissue sarcoma (Fan et al.). Recent studies showed that tumor cells expressing MDR-associated protein (MRP) (Cole et al., 1992), lung resistance protein (LRP) (Scheffer et al., 1995) and mutation of DNA topoisomerase II (Beck, 1989) also may render MDR.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Anand, 1992; Guthrie and Fink, 1991; Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book, A guide for the laboratory use of zebrafish (Danio rerio)*, (4th Ed., Univ. of Oregon Press, Eugenie, 2000).

EXAMPLES

The present invention is described by reference to the following Examples, which are offered by way of illustration and are not intended to limit the invention in any manner. Standard techniques well known in the art or the techniques specifically described below were utilized.

Example 1 siRNA Site Selection and Design

The siRNA was designed to target a highly accessible site in the HIV-1 rev transcript as previously reported (Lee et al., 2002). The shRNA design involved extending the sense strand by eight nucleotides on the 3' end to obtain a 28-nucleotide stem. A single C to U point mutation was designed in the center of the sense strand to facilitate cloning. The sequence of the 9 base loop was described previously by Xia et al. (2002).

Example 2

Constructs

Construction and characteristics of the plasmid pIND RevEGFP have been previously described (Lee et al., 2002). In order to create the vector pIND-shRNA, two PCR reactions were carried out.

A) The pIND promoter was amplified by PCR using primers that would amplify the promoter alone, or the promoter plus the 5' leader sequence from the pIND vector (Invitrogen).

B) For PCR amplification of shRNAmpolyA, two overlapping oligonucleotides were designed:

(SEQ ID NO: 2)
5'-GCCTGTGCCTCTTCAGTTACCGCTTGAGTTCAAGAGACTCAAGCGGT
AGCTGAAGAGGCACAGGCTTCTAGAACTAGTAATAAAGGATCC-3'

-continued (SEQ ID NO: 3)
5'-CGGTCTAGACGCGGCCGCACACAAAAAACCAACACACGGATCCAATG
AAAATAAAGGATCCTTTATTACTAGTTCTAGAAGC-3'.

These were annealed and primer extended in the presence of dNTPs and further amplified by PCR.

The PCR products from both of the above reactions were blunt end ligated to one another and cloned in the pCR2.1 vector (Invitrogen). The construct without the leader element was designated as mpIND-shRNAmpolyA and the construct with the leader element was called pIND-shRNAmpolyA.

Figure 2A:
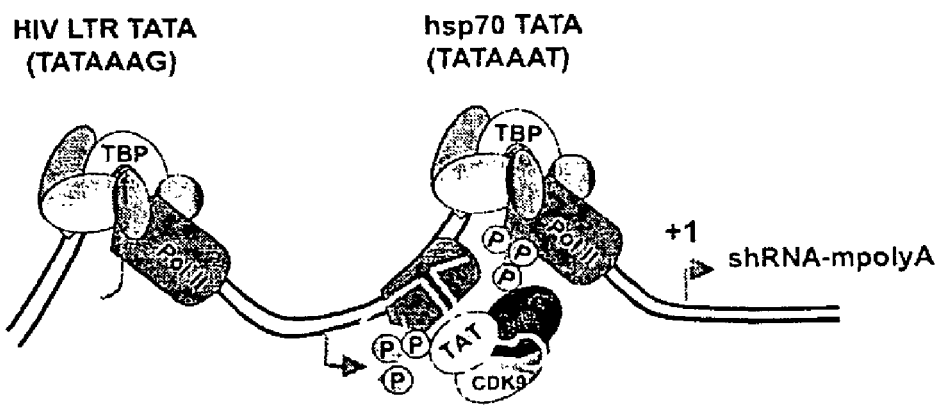
FIG. 2A shows a schematic representation of LTRhsp-shRNA. HIV-1 LTR along with the TAR loop region was cloned upstream of the minimal hsp70 promoter.

For construction of the LTRhsp-shRNA, the E/GRE elements were removed from the mpIND-shRNAmpolyA construct using Bgl II and Xma I and the pNL4-3 derived HIV-1 LTR was inserted in the same position (FIG. 2A). The hsp70 TATA mutant construct was obtained by mutating the hsp70 TATA box to a Cla I site.

Construction and characteristics of the lentiviral vector pHIV-7 have been previously described (Gasmi et al., 1999). For pHIV-LTRhsp-shRNA, the entire LTRhsp-shRNA along with the minimal polyA signal sequence was PCR amplified and cloned in Not I and BstE II sites of pHIV-7 in the reverse orientation.

Example 3

Cell Culture

ECR-293 cells were obtained from Invitrogen and maintained according to the supplier's instructions. HT1080 and 293 Cells were maintained in DMEM 20% FBS. Twenty-four hours before transfection, cells were replated in 6-well plates at 50-70% confluency with fresh medium without antibiotics. The Human T cell Line CEM was maintained in RPMI1640 medium supplemented with 10% FBS. For co-transfection, the target (either pIND RevEGFP or pNL4-3) was used in a 1:2 weight/weight ratio with the shRNA constructs and transfection was carried out using Lipofectamine Plus (Gibco-BRL) according to the manufacturer's instructions. For induction of the rev-EGFP or shRNA construct, 5 M ponasterone A (Invitrogen) was added to the cell culture. Two days post induction, the transfected cells were visualized by fluorescent microscopy. Images were collected using an Olympus BX50 microscope and DEI-750 video camera (Optronics) at 40× magnification with an exposure time of ¼ sec. Specific silencing of target genes was confirmed in at least three independent experiments.

Example 4

Northern Blotting

Total RNA was extracted using RNA STAT-60 (TEL-TEST "B") according to the manufacturer's instructions. 15 µg of total RNA was electrophoresed in a 10% polyacrylamide/8M urea gel. RNA was transferred by electroblotting onto a Hybond-N+ membrane (Amersham Pharmacia Biotech). The hybridization was performed using an oligonucleotide probe complementary to the antisense strand of the siRNA. Hybridizations were carried out at 37° C. and the filters were washed twice with 2×SSPE at 39° C. and then once with 1× SSPE at 41° C. prior to autoradiographic exposure.

Example 5

Figure 3A:
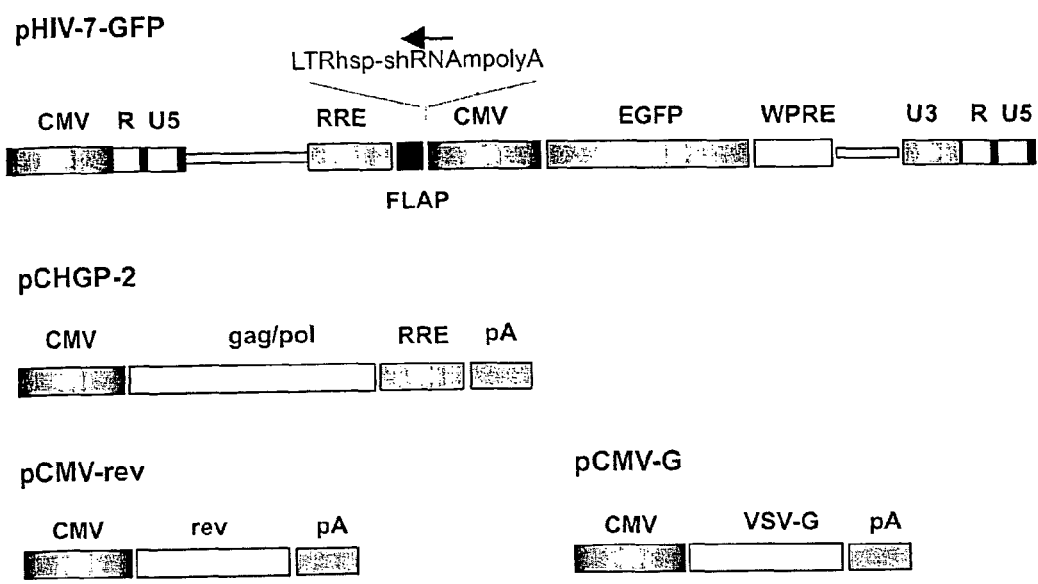
FIG. 3A shows a schematic representation of a packaging system useful for inhibition of HIV-1 replication. The lentiviral vector, pHIV-7-GFP, contains a hybrid 5' LTR in which the U3 region is replaced with the CMV promoter, the packaging signal (Ψ), the RRE sequence, the EGFP gene driven by CMV promoter, and the 3' LTR in which the cis regulatory sequences are completely removed from the U3 region. LTRhsp-shRNA mpolyA is inserted directly upstream of the CMV promoter of EGFP in pHIV-7-GFP vector in the reverse orientation. The solid box between RRE and CMV-EGFP represents the FLAP sequence of HIV-1. pCHGP-2 contains the gag and pol genes and RRE sequence from HIV-1 under the control of the CMV promoter. pCMV-Rev contains the coding sequence of Rev driven by the CMV promoter. pCMV-G contains the VSV-G protein gene under the control of the CMV promoter. pA indicates the polyadenylation signal from the human β-globin gene.

Lentiviral Vector Production 293T cells were cultured until they reached 80% confluency in a 100 mm culture dish. 15 µg of lentiviral vector with the appropriate insert, 15 µg of pCHGP-2, 5 µg of pCMV-G and 5 µg of pCMV-Rev were cotransfected into 293T cells using the calcium phosphate precipitation procedure (Graham and van der Eb, 1973). The packaging system is shown in FIG. 3A (Gasmi et al., 1999). Six hours after transfection, the culture medium was replaced. The culture supernatants were collected at 24 h and 36 h after transfection. The supernatants were pooled together, passed through a 0.45 µm filter, concentrated by ultracentrifugation and stored at −80° C. until use. Vector titers were determined by transduction of HT1080 cells and assayed for EGFP expression using flow cytometry. The vectors were free of replication competent lentivirus as determined by both RT-PCR and p24 antigen assays.

Example 6

Transduction of Target Cells

To transduce CEM T cells, 2×10$^5$ cells were placed in a 15 ml centrifuge tube with 1 ml culture medium in the presence of lentiviral vector at a moi of 10.0 and 8 µg/ml polybrene. Following centrifugation at 2000 rpm for 1 h, the cells were transferred into a 24 well culture plate and after 24 h the culture medium was replaced. For transduction of CD34+ cells, CD34+ stem cells were enriched from umbilical cord blood by anti-CD34+ antibody-coupled magnetic beads (Miltenyi Biotech, Aubum, Calif.). The purity of CD34+ cells was above 90% as determined by FACS analysis. After overnight culture in Iscove's modified Dulbecco's medium (IMDM) supplemented with 20% FBS, IL-3 (10 ng/ml), IL-6 (10 ng/ml) and SCF (10 ng/ml) in fibronectin-treated plates, the cells were transduced with lentiviral vectors at a moi of 40.

Example 7

HIV-1 Challenge

Twenty-four hours after transduction, 1×10$^6$ CEM-T cells were infected with HIV-1 strain IIIB at a moi of 0.005. After overnight incubation, the cells were washed three times with Hanks' balanced salts solution (HBSS) and cultured in medium with R10 (RPMI 1640+10% FBS) for CEM-T cells. At designated days, cell culture supernatant was collected for HIV-1 p24 antigen analysis. For challenges of CD34 stem cells, lentiviral vector-transduced CD34+ cells were propagated in IMDM containing 20% FBS, IL-3 (10 ng/ml), IL-6 (10 ng/ml), and SCF (10 ng/ml) on irradiated human stroma cells for one week. 2×10$^5$ CD34+ cells were exposed to JR-FL strain of HIV-1 at a moi of 0.01 overnight. The infected cells were washed four times with HBSS and the cultures were continued in the medium containing the cytokines. At designated days, cell culture supernatant was collected for HIV-1 p24 antigen analysis.

Example 8

HIV-1 Antiviral Assays

Cells were co-transfected with HIV-1 proviral DNA pNL4-3 and the appropriate shRNA constructs. Culture supernatants were collected at twenty-four hour intervals and analyzed for HIV-1 p24 antigen using an ELISA assay (Beckman Coulter Corp). The p24 values were calculated using a Dynatechi MR5000 ELISA plate reader (Dynatech Lab Inc).

Cell viability was also performed using a Trypan blue dye exclusion count 4 days post transfection.

Example 9

Demonstration of Expression of shRNA from Pol II Promoter

To demonstrate expression of shRNA from a Pol II promoter, an shRNA consisting of a 28 base pair stem with a 9 base loop specifically targeted to HIV-1 rev was inserted downstream of the ponasterone A inducible promoter (pIND) in two different Pol II expression cassettes, with or without the 5' leader element of the minimal hsp70 promoter from the pIND vector (FIG. 1A). A minimal polyA sequence was included as previously described (Xia et al., 2002). According to one publication, the 5' hsp leader element is essential for the transcriptional elongation block observed with the *Drosophila* hsp70 promoter (Lee et al., 1992). It was therefore assumed that removal of the leader sequence from the transcripts would allow functional shRNA expression, but would eliminate the inducibility of the system. It was further assumed that the complete pIND construct would be inducible by ponasterone A but would contain a long leader sequence which would have to be processed to produce a functional sh/siRNA. Since the shRNA contains a stem of 28 base pairs, it was possible that the entire transcript would be a Dicer substrate, thereby making siRNA production inducible.

Example 10

Assaying siRNA

Figure 1B:
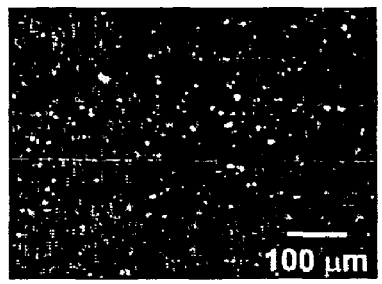
FIG. 1B are photographs showing inhibition of RevEGFP expression by shRNAs. EcR-293 cells were co-transfected with pIND-RevEGFP and shRNA constructs in the presence and absence of ponasterone, as indicated. Cells were examined microscopically for EGFP expression as described in the Examples. The right panels in all cases are phase contrast images taken at the time of fluorescent microscope analysis (left panels) showing that approximately equivalent numbers of cells are present in each field. Cells transfected with shRNA construct without the leader element removed showed an approximate 90% reduction in fluorescent cells. Cells transfected with pIND-shRNA showed EGFP expression levels similar to that observed with cells transfected with only the Rev-EGFP construct. Specific silencing of Rev-EGFP was confirmed by at least three independent experiments.
Figure 1B:
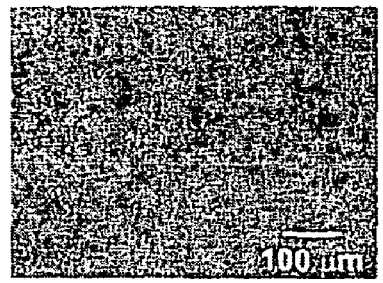
Figure 1B:
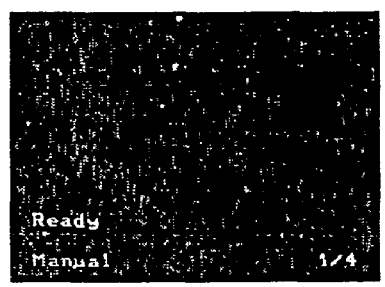
Figure 1B:
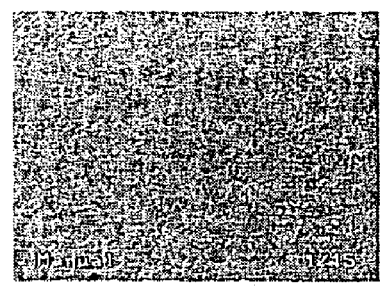
Figure 1B:
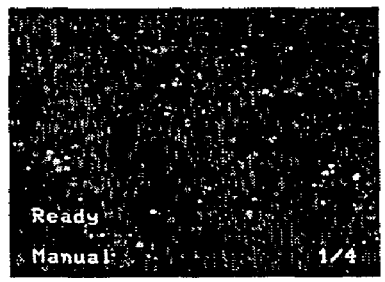
Figure 1B:
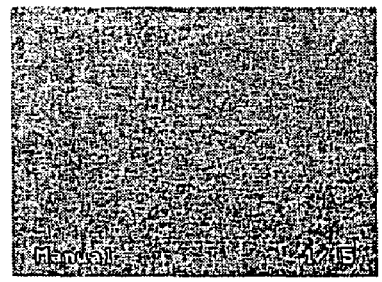
Figure 1B:
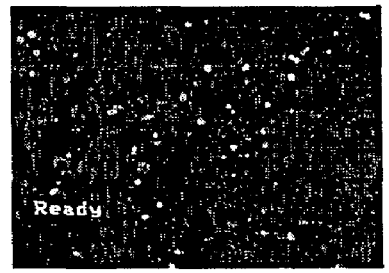
Figure 1B:
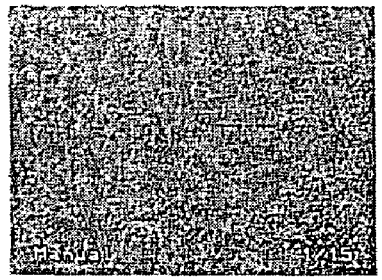

In order to assay the siRNAs, the HIV-1 Rev gene was fused to EGFP and expressed in the pIND vector system. EGFP fluorescence was observed as early as 3 hours post addition of the inducer ponasterone A and continued for more than 100 hours. EcR-293 cells were co-transfected with the various shRNA expression constructs and pIND-REV-EGFP. EcR-293 cells are modified HEK 293 cells that stably express the ecdysone receptor and are inducible by the ecdysone analog ponasterone A. Sixteen to twenty hours post transfection, ponasterone A was added to induce the expression of both the shRNA constructs as well as the target rev-EGFP RNA. The cells were incubated for an additional 48 hours prior to fluorescent microscopic analysis. As seen in FIG. 1B, the shRNA construct lacking the leader element resulted in pronounced inhibition of the EGFP signal relative to the control construct. In contrast, the shRNA construct harboring the hsp70 leader gave no inhibition. Cells transfected with an irrelevant shRNA construct also showed no inhibition of Rev-EGFP.

Example 11

Determining Expression and Processing of shRNA

Figure 1C:
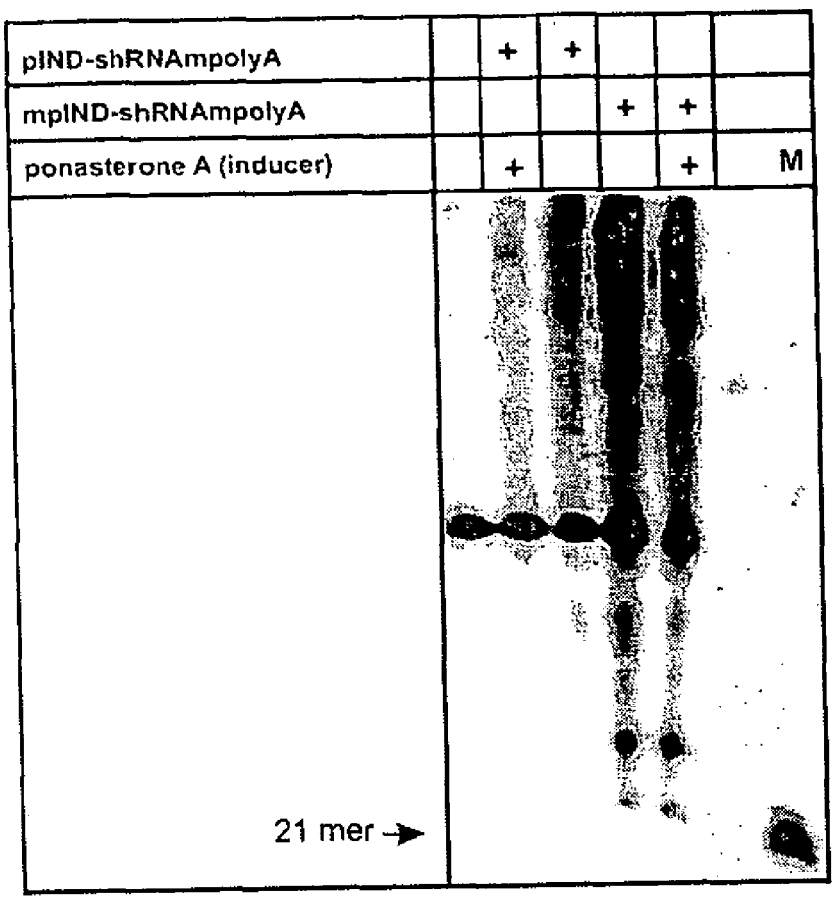
FIG. 1C shows results of a Northern blot analysis of EcR-293 cells transfected with shRNA constructs in the presence and absence of ponasterone, as indicated. mpIND-shRNAmpolyA construct showed expression and processing to siRNA-sized products, both in the presence and absence of the inducer while the construct with the leader element showed no processing even in the presence of the inducer. Upper arrow indicates primary transcript region, the lower bands indicate partially processed hairpin and siRNAs, respectively. The strong band in all lanes is an unknown cellular transcript that has homology to the oligonucleotide probe. M=Marker (21 nucleotide RNA).

To determine whether or not the shRNA was being expressed and processed to siRNA-sized products, ECR-293 cells were transfected with the various shRNA constructs. Seventy-two hours post-transfection, RNAs were isolated from cells either treated or untreated with the inducer ponasterone A and Northern gel analyses were carried out. The mpIND-shRNAmpolyA construct lacking the hsp leader element, whether grown in the presence or absence of ponasterone A, resulted in readily detectable RNAs of the size expected from partially processed and fully processed shRNAs (FIG. 1C). The construct in which the leader element was retained shoved inducible expression of a long, unprocessed RNA precursor, but no siRNA sized products. This would be expected as *Drosophila* hsp70 transcription is controlled by proximal promoter pausing where elements both upstream and downstream of the TATA box play a role. Deletions downstream of the TATA box would abolish pausing which however can be restored by duplicating a sequence upstream of the hsp70 TATA box (Lee et al., 1992).

Example 12

Demonstration of Functional Inhibition of HIV-1

Figure 1D:
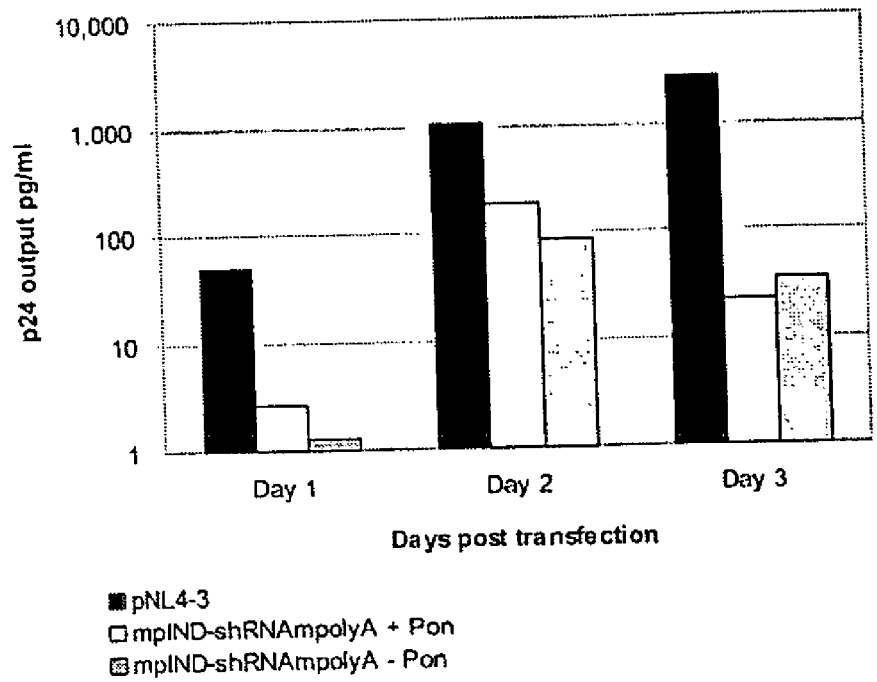
FIG. 1D is a graph showing inhibition of HIV-1 gene expression by shRNA constructs. EcR-293 cells were co-transfected with wild type infectious proviral DNA, pNL4-3 and mpIND-shRNAmpolyA in the presence and absence of ponasterone, as indicated. Inhibition is seen both in the presence and absence of the inducer.
Figure 1E:
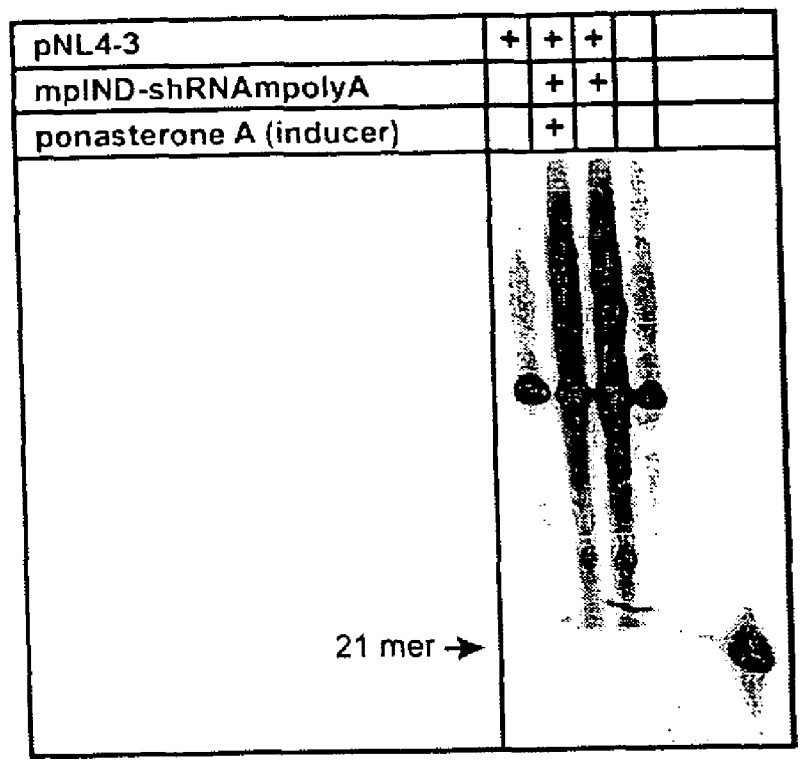
FIG. 1E shows results of a Northern blot analysis of total RNA extracted from the above cells and shows that siRNA expression and processing occurs both in the presence and absence of the inducer. The arrows indicate partially processed and fully processed shRNAs and siRNAs, respectively. The strong band in all lanes is a cellular transcript that has homology to the oligonucleotide probe.

Functional inhibition of HIV-1 in transient co-transfection assays by the shRNA constructs was demonstrated by co-transfecting ECR-293 cells with HIV-1 pNL4-3 proviral DNA and mpIND-shRNAmpolyA in the presence or absence of ponasterone A. Culture supernatants were collected and ELISAs for HIV-1 p24, a reliable indicator of HIV infection, were carried out. Cells transfected with mpIND-shRNAmpolyA resulted in about 2 logs of inhibition of HIV-1 p24 expression relative to the control vector. Addition of the inducer ponasterone A did not enhance the anti-HIV-1 activity to any significant extent (FIG. 1D). Northern gel analyses of these cells showed that the shRNA was readily detectable and processed to siRNA-sized products both in the presence and absence of ponasterone A (FIG. 1E).

Example 13

Devised Expression Strategy

A number of studies with RNA based antivirals have shown that ribozymes and antisense RNA when expressed from the HIV LTR can efficiently inhibit viral replication in cells infected with HIV (Dropulic et al., 1996; Paik et al., 1997). The expression depends on the presence of the viral transactivator protein TAT which binds to the TAR loop and recruits P-TEFb (P-transcription elongation factor b), a heterodimer of CDK9 and cyclinT1, which in turn phosphorylates the CTD of RNA polymerase and makes it elongation competent (Karn, 1999; Kabor and Greenblatt, 2002). However, it has been previously demonstrated (Xia et al., 2002) and confirmed that shRNAs with appended, non-target derived 5' extensions do not function effectively in RNAi.

To circumvent this problem, an expression strategy was devised that results in the first base of the transcript being the first base of the shRNA. This approach exploits the striking similarities reported between the *Drosophila* hsp70 promoter and the HIV-1 LTR and the fact that the hsp70 core promoter is receptive to a variety of activators (Brand and Perrimon, 1993; No et al., 1996). Both of these promoters show significant similarities in the region flanking their TATA boxes and both the promoters are regulated by promoter proximal pausing which can be relieved by P-TEFb kinase (Krumm et al., 1993). Both the HIV-1 LTR and hsp70 promoter show similar kinetics when activated with heat shock (Kretz-Remy and Arrigo, 1994). It was therefore reasoned that the hsp70 promoter might be regulated by TAT binding to an upstream TAR element.

Example 14

Creation of Inducible System to Respond to HIV Infection in an effort to create an inducible system that would respond to HIV infection, the hsp70 core promoter and the shRNAmpolyA cassette from the mpIND-shRNAmpolyA were inserted downstream of the HIV-1 LTR up to and including the TAR sequences (FIG. 2A). It was anticipated that transcription from the HIV-1 LTR might stall following transcription of the TAR loop (Palangat et al, 1998) and immediately upstream of the initiation complex assembled at the downstream hsp70 promoter. It is also known that in the case of both promoters, recruitment of negative transcription elongation factors (N-TEF) consisting of negative elongation factor (NELF) and DRB sensitivity inducing factor (DSIF) suppresses basal transcription (Chwen-Huey et al., 2003; Fujinga et al., 2004). The TAR loop is known to recruit N-TEF, which suppresses transcription from both promoters (Mason and Lis, 1997). HIV-1 TAT bound to the TAR element upstream of the hsp70 core promoter would recruit P-TEFb, which not only phosphorylates the RD subunit of NELF (Fujinga et al., 2004) and causes the release of N-TEF, but also in turn could phosphorylate the C terminal domain (CTD) of the RNA polymerase complexed with the hsp70 initiation complex. Phosphorylation of RNAP should relieve this elongation block. The resulting transcript should initiate at position +1 of the shRNA.

Example 15

Cotransfection with shRNA Containing Construct and TAT Containing Plasmid

Figure 2B:
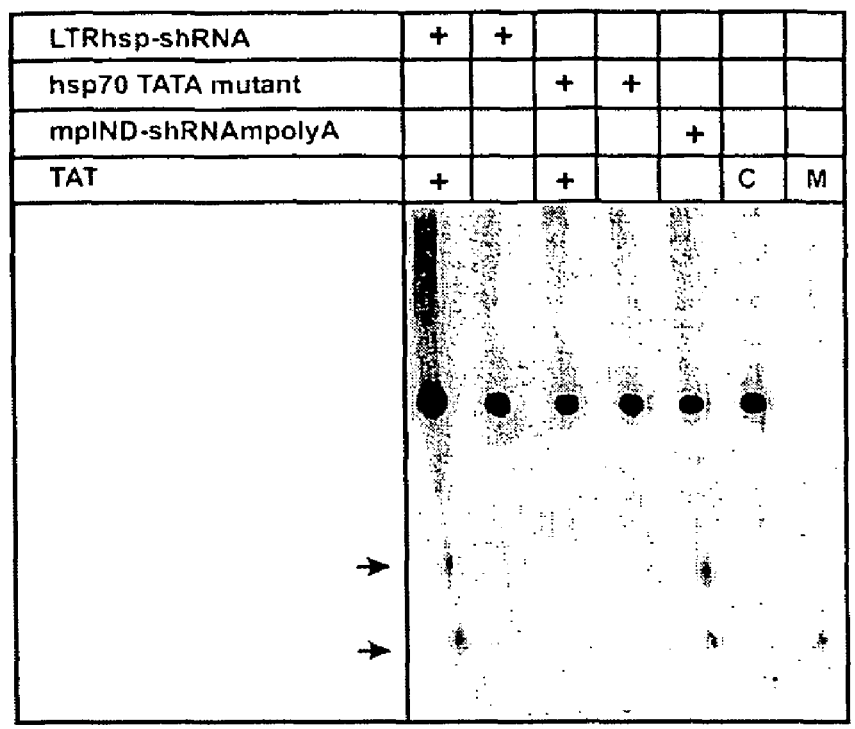
FIG. 2B shows results of a Northern blot analysis of 293 cells and shows Tat inducible expression of shRNAs. Cells were co-transfected with LTRhsp-shRNA or the hsp70 TATA mutated construct in the presence or absence of a Tat expressing plasmid, as indicated. Expression and processing to siRNA-sized products was only observed in the presence of Tat. The hsp70 TATA mutated construct did not show any processing. mpIND-shRNAmpolyA was transfected as a Pol II expressed shRNA control. Arrows indicate partially processed precursor and siRNA sized products. The strong band common to all lanes is an endogenous sequence with homology to the antisense olignucleotide probe. C=Cell control; M=Marker (21 nucleotide RNA).

To test the above, 293 cells were co-transfected with the LTRhsp-shRNA construct in the presence and absence of a plasmid expressing TAT fused to dsRed1. 72 hours post transfection, the cells were visualized by fluorescence microscopy. Fluorescent microscopic examination of these cells revealed about 80% transfection efficiency showing that TATdsRed was efficiently expressed in transfected cells (data not shown). Northern blot analyses of the transfected cells shows that the shRNA was expressed and processed to siRNA-sized products only in the presence of TATdsRed1 (FIG. 2B). To verify that transcription from the hsp70 core promoter and not the HIV-1 LTR resulted in expression of the active siRNA-sized products, a construct was created and tested in which the hsp70 TATA box was mutated to an inactive form. When the vector harboring this promoter was tested for shRNA expression, no shRNA or siRNA-sized products were detected in the presence and absence of Tat. These results demonstrate that transcription preferably be initiated from the hsp70 TATA box in order to be functionally processed into an siRNA. Transcripts originating from the HIV-1 LTR would have an additional TAR loop at the 5' end of the sense strand which would impede recognition and processing to siRNAs.

Example 16

Cotransfection Studies

Figure 2C:
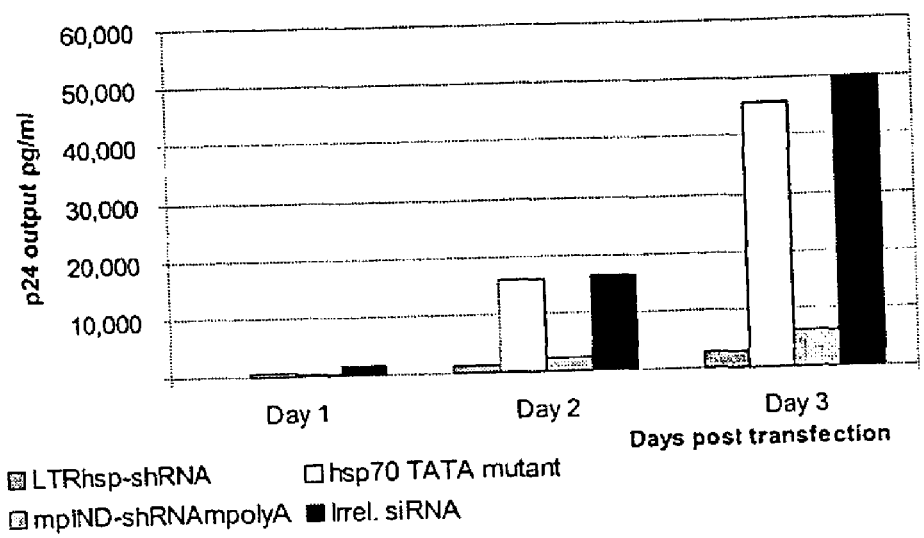
FIG. 2C is a graph showing Inhibition of HIV gene expression by LTRhsp-shRNA. 293 cells were co-transfected with pNL4-3 and fold decrease in HIV-1 p24 is observed in cells transfected with LTRhsp-shRNA. The level of inhibition was comparable to that observed with mpIND-shRNAmpolyA which was used as Pol II expressed shRNA control.
Figure 2D:
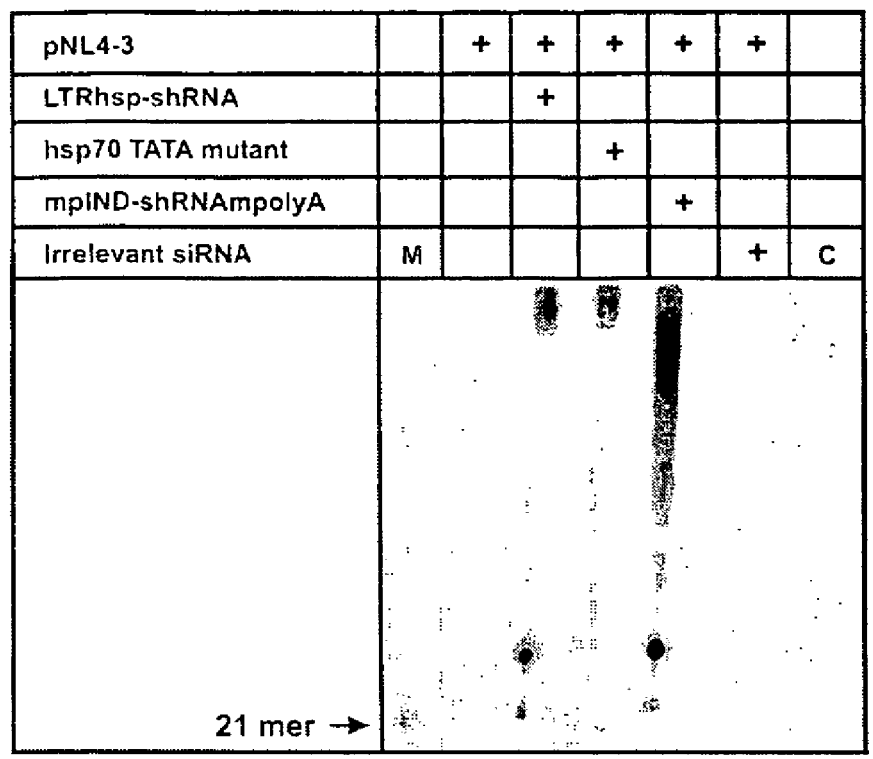
FIG. 2D shows results of a Northern blot analysis of total RNA extracted from the above cells and shows efficient expression and processing in cells transfected with LTRhsp-shRNA and mpIND-shRNAmpolyA. The siRNA sized products are indicated, the band above these is the partially processed shRNA. C=Cell control; M=Marker (21 nucleotide RNA).

To better estimate the extent to which the LTRhsp-shRNA was effective against HIV replication, pNL4-3 proviral DNA was transiently co-transfected with the various shRNA constructs into HEK 293 cells. HIV replication was assessed by ELISAs for HIV-encoded p24 in culture supernatants. As can be seen from FIG. 2C, there was an approximate 90% inhibition of HIV-1 gene expression mediated by the LTRhsp-shRNA construct relative to cells transfected with pNL4-3 and irrelevant siRNA, which is comparable to the inhibition observed with the shRNA expressed from mpIND-shRNAm-polyA construct. The hsp70 TATA mutant failed to show any inhibition. Northern blot analyses of the RNAs from these transfections showed that the shRNA/siRNA was induced in the presence of HIV-1 pNL4-3 (FIG. 2D). This result demonstrates HIV-1 infection is sufficient to induce shRNA expression from the LTRhsp-shRNA construct. In this setting, expression of TAT functions as part of a negative feedback loop that results in transcriptional activation of the anti-rev siRNA. The negative control for these experiments is the mutant hsp70 TATA box construct from which no detectable shRNA/siRNAs were produced.

Example 17

Cotransfection Studies

Figure 4:
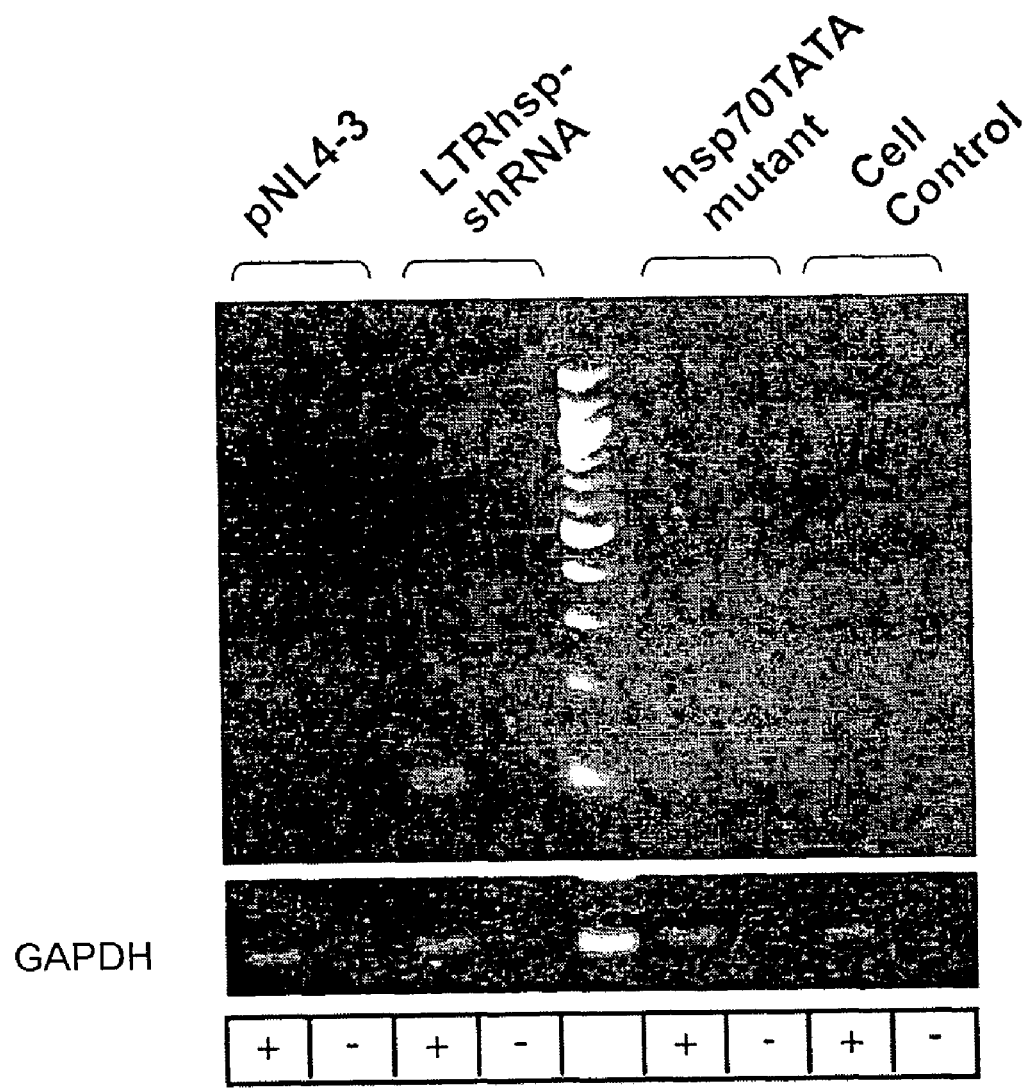
FIG. 4 is a gel photograph showing transcription occuring from both HIV-1 LTR and mhsp70 TATA boxes. 293 cells were co-transfected with pNL4-3 and LTRhsp-shRNA or hsp70 TATA mutant. 50 ngs of Total RNA was used for RT-PCR analysis using primers flanking the HIV-1 TAR and hsp70 TATA box sequences. Lanes corresponding to the LTRhsp-shRNA and the hsp70 TATA mutant showed signals of similar intensity. GAPDH was amplified as an internal control.

According to one report, the HIV-1 TATA box is constitutively bound by the TATA binding protein (TBP) and TBP-associated factors (TAFs) (Mason and Lis, 1997). This binding might serve as a 'roadblock' to transcription originating from the HIV-1 LTR and would cause arrest or at least a decrease in productive transcription from the HIV-1 LTR. To test if this was so and whether the hsp70 initiation complex served as a transcription roadblock, 293 cells were co-transfected with pNL4-3 and the LTRhsp-shRNA or hsp70 TATA mutant construct. Total RNA was extracted and RT-PCR analysis was carried out using a 5' primer complementary to the TAR loop and a 3' primer designed to hybridize with the sequence between the hsp70 TATA box and shRNA transcription start. If the TAFs at the hsp70 TATA served as a 'roadblock' to transcription from the HIV LTR, there would be a decrease in the RT-PCR signal relative to the signal obtained using RNA from the hsp70 TATA mutant construct. As seen in FIG. 4, both lanes gave a similar RT-PCR signal after compensating for the internal standard GAPDH signal.

Thus, this data does not support a 'roadblock' model as suggested for some genes regulated by dual promoters or TATA boxes. In those situations, the majority of the transcripts originate from the downstream promoter such as has been reported for the human fatty acid synthase gene (Hsu et al., 1996). This data supports a model wherein the hsp70 initiation complex is phosphorylated as a 'bystander' due to the P-TEFb, which is recruited in close proximity by the TAT-TAR interaction. It has been shown that a strong transcription pause delays human RNAPII at the base of the TAR loop (position +62) (Palangat et al., 1998). This pause is independent of the promoter proximal pausing and would occur even in presence of TAT. The pause, with a half-life of about 22 seconds, is due to the formation of a hairpin structure which causes the RNAP to reverse translocate by 2 nucleotides. This allows time for the assembly of the initiation complex at the downstream hsp70 promoter. This pausing is important to the system as attempts to abolish the pausing by activating transcription from the HIV-1 LTR via the NF-κB pathway reduced transcription from the hsp70 promoter by a factor of 2 (data not shown).

Figure 5:
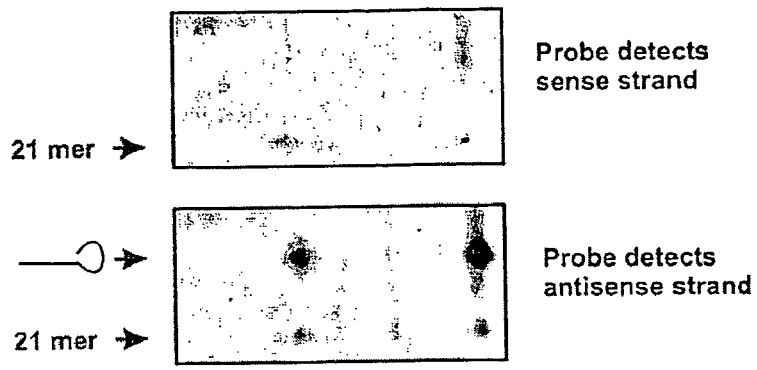
FIGS. 5A and 5B show partial processing of an shRNA loop.
Figure 5:
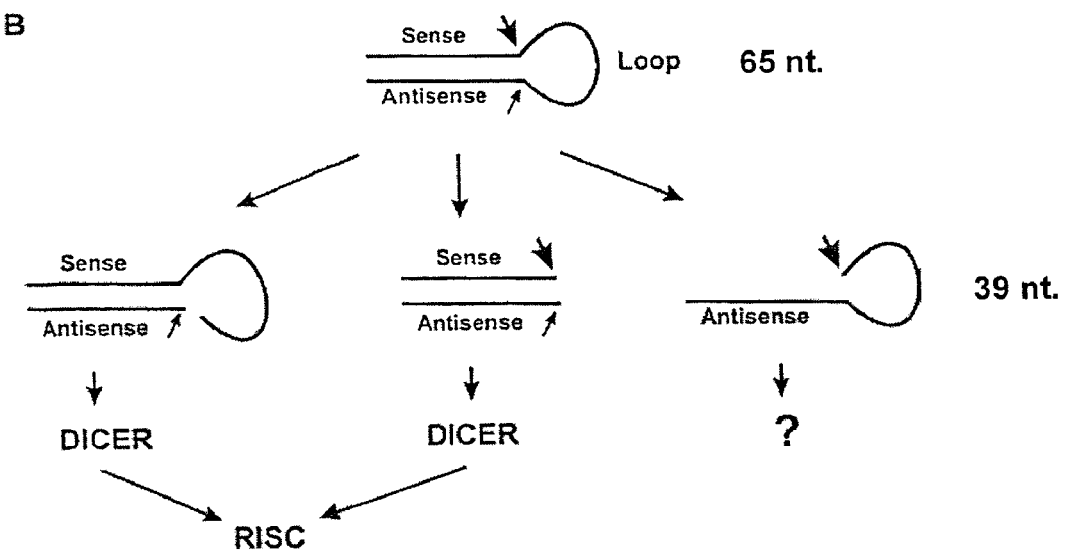

In a preferred embodiment, the short hairpin RNA expressed from the various promoters consists of two 28 base arms separated by a 9 base loop sequence. Thus, an shRNA that is processed fully from the 3' end should result in a transcript that is ~65 bases in length. When the probe used was complementary to the antisense strand, the partially processed hail-pill seen in FIG. 5A, was determined to be ~39-40 bases. This product was not detectable when a probe complementary to the sense strand was used, suggesting a partial processing of some shRNA molecules in which a cleavage eliminates the sense strand, leaving behind the antisense plus all or most of the loop (FIG. 5B). This intermediate appears to accumulate to relatively high levels relative to the fully processed siRNAs. At this time it is not known if the partially processed shRNA is a dead end product or an siRNA precursor.

Example 18

Use of Inducible System in Gene Therapy Setting

Figure 3B:
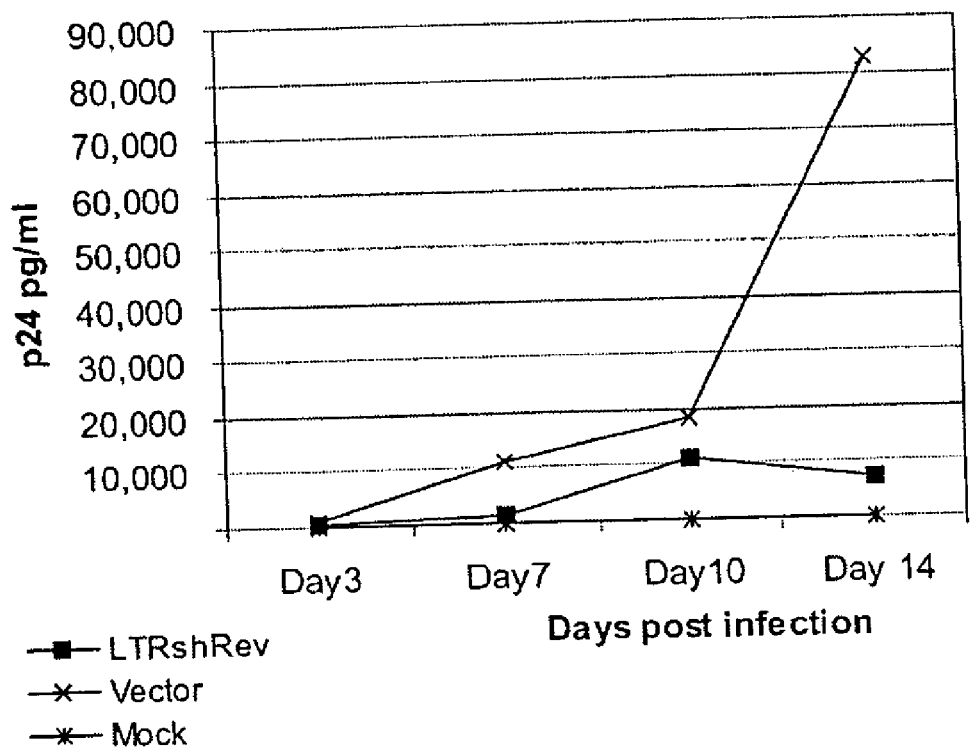
FIGS. 3B and 3C show the results of an HIV-1 challenge assay. CD34 stem cells or CEM cells transduced with pHIV-7-LTRhspshRNA were challenged with a JRFL or HIV-1 IIIB strain, respectively. Culture supernatants were collected and p24 ELISA was carried out as described in the Examples. LTRshREV=LTRhsp-shRNA cloned in the reverse orientation.
Figure 3C:
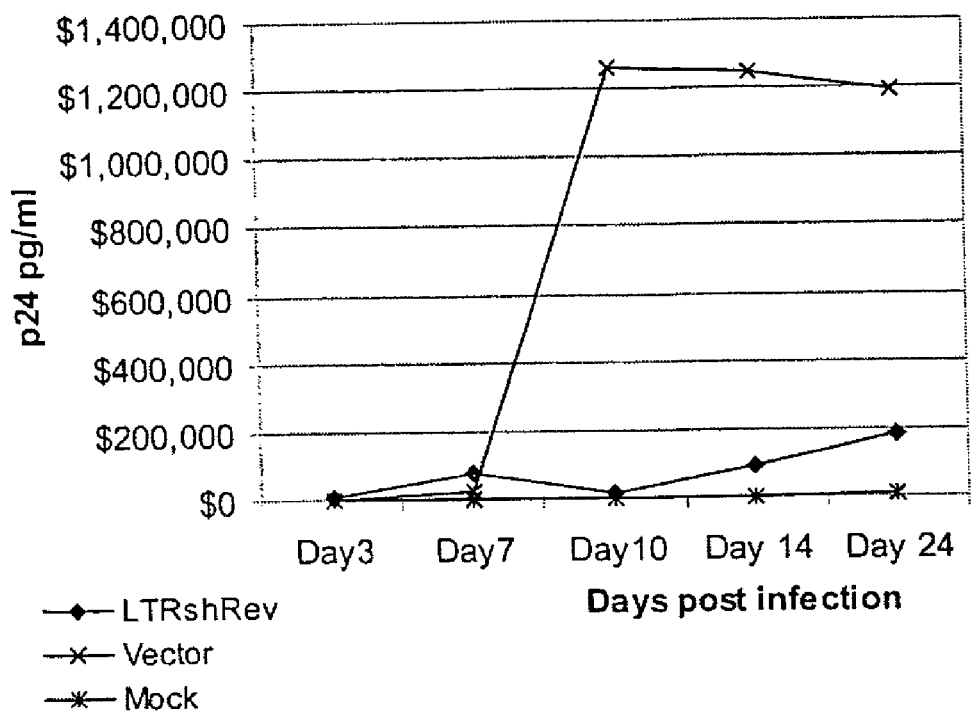

To show that the present invention is useful in a more stable gene therapy setting, the LTRhsp-shRNA construct was cloned in pHIV-7 in the reverse orientation. When 293 cells were co-transfected with pNL4-3 and LTRhsp-shRNA in pHIV-7, HIV inducible siRNA expression was observed from this construct in a transient transfection assay (data not shown). Primary CD34+ hematopoietic stem cells and CEM T cells were transduced with the LTRhsp-shRNA construct cloned in pHIV-7. The transduced cells were infected with HIV-1 JRFL or HIV-1 IIIB, respectively, at an MOI of 0.005. Culture supernatants were collected at different time points and analyzed for p24 levels by ELISA. As seen in FIGS. 3B and 3C, 85% and 92% inhibition of p24 levels were observed in CEM T cells and CD34 stem cells, respectively, transduced with pHIV-LTRhsp-shRNA as compared to vector backbone transduced cells.

Figure 6:
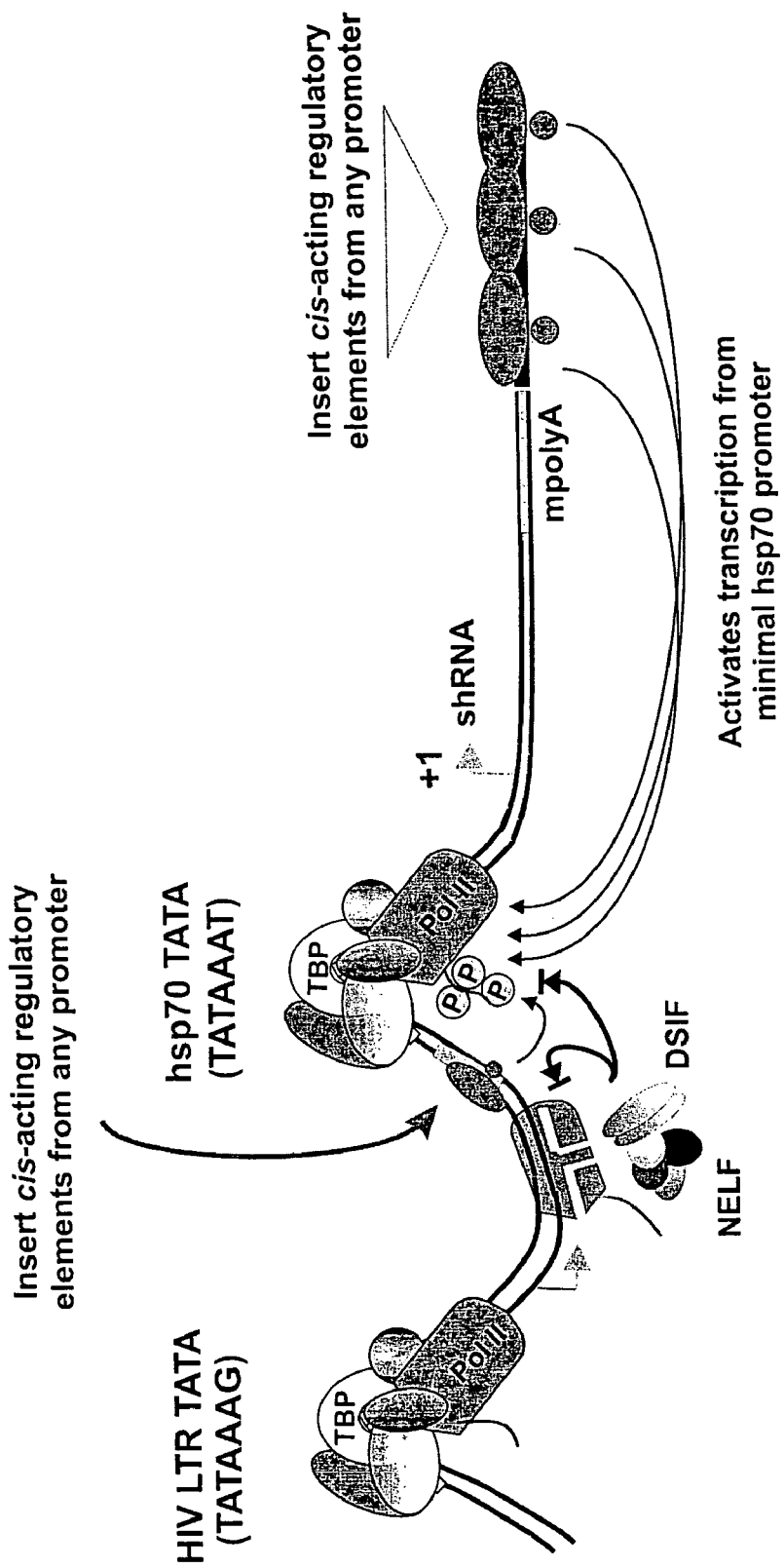
FIG. 6 is a schematic representation of a general inducible system using a fusion promoter according to the invention. The cis-acting regulatory elements are cloned either between the TAR loop and the minimal hsp70 promoter, as shown, or downstream of the minimal polyadenylation signal sequence (mpolyA). Transcription of the TAR loop by the HIV-1 LTR recruits N-TEF components NELF (tetramer) and DSIF (dimer). These in turn suppress transcription from the hsp70 promoter as well as HIV-1 LTR. Binding of cis-acting transcriptional activators either downstream of the minimal polyA or between the TAR loop and the minimal hsp70 promoter activates shRNA transcription from the hsp70 promoter.

The fusion promoter of the present invention is believed to be the first report of an HIV-1 inducible siRNA system. Earlier studies have shown that TAT can transactivate heterologous promoters when the TAR element is placed downstream of the promoter (Hall et al., 1991). A TAT-GAL4 fusion protein has also been shown to activate transcription from downstream promoter elements when targeted to upstream Gal4 binding sites (Southgate and Green, 1991). The present invention thus is believed to provide the first demonstration of a TAR element upstream of a basal promoter element for activation of transcription from the basal promoter. By expressing HIV-1 TAT from an inducible promoter, in one embodiment, the present invention offers a system for inducible expression of a variety of shRNAs, including those to cellular and viral targets. In a preferred embodiment, a cis-regulatory element of viral or cellular origin can be cloned between the TAR element and the hsp70 promoter or downstream of the minimal polyA, as shown in FIG. 6. The HIV-1 LTR would still be used to transcribe the TAR loop, whose function would be not as a transcriptional activator by recruiting TAT, but as a repressor by recruiting N-TEF. N-TEF would suppress the transcription from the hsp70 promoter, as was seen in studies of the system of the invention. Additionally, binding of viral specific or tissue specific transcription factors to the cis-regulatory elements inserted in either of the two places above, as shown in FIG. 6, could phosphorylate the C terminal domain (CTD) of the RNA polymerase complexed with the hsp70 initiation complex. Phosphorylation of RNAP should relieve this elongation block. Using this approach one can use this promoter for inducible expression of siRNA in response to, for example, tissue specific, viral, cellular or engineered transcription factors. For example, in one embodiment, an ecdysone inducible system could be achieved by cloning ecdysone response elements in either of the above places (i.e., between the TAR element and the hsp70 promoter or downstream of the minimal polyA, as shown in FIG. 6).

Several studies have focused on inducible Pol III siRNA expression systems (Wiznerowicz and Trono, 2003; Matsukura et al., 2003; van de Wetering et al., 2003) as constitutively expressed siRNAs have to compete with endogenous micro RNAs and also to minimize the possibilities of off-target and interferon effects (Moss and Taylor, 2003; Sledz et al., 2003; Bridge et al., 2003). Since it is unknown what the long term effects of constitutive expression of short hairpin RNAs might have on the micro RNA machinery and the genes these micro RNAs regulate, an inducible system would provide a level of safety that may be required for long term gene therapy treatment of HIV-1 infection in a gene therapy setting. In particular, a drug inducible system, although useful in a research setting, may not be practical in a therapeutic setting, as every cell harboring the siRNA construct would express siRNA oil administering the drug. From the perspective of safety in a gene therapy setting, the system of the present invention could be used to activate anti-HIV-1 sh/siRNAs only in cells infected by an active virus thereby eluding potential toxicities that may ensue with long term expression of sh/siRNAs in a therapeutic setting.

Several studies have focused on the need to use an HIV inducible setting to express their anti-HIV genes (Dropulic et al., 1996; Paik et al., 1997). The fusion promoter system of the invention provides the safety of an HIV-1 inducible system without comprising the efficacy of the antiviral shRNA. Moreover, in a further embodiment the TAT inducible system can be utilized for regulated siRNA production against cellular targets by making the TAT expression system itself inducible.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use or any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

An, D. et al. (2003). Efficient lentiviral vectors for short hairpin RNA delivery into human cells. *Hum Gene Ther* 14:1207-1212.

Berkhout, B. et al. (1989). Tat trans-activates the human immunodeficiency virus through a nascent RNA target. *Cell* 59:273-282.

Brand, A. and Perrimon, N. (1993). Targeted gene expression as a means of altering cell fates and generating dominant phenotypes. *Development* 118:401-415.

Bridge, A. et al. (2003). Induction of an interferon response by RNAi vectors in mammalian cells. *Nat Genet* 34:263-264.

Brummelkamp, T. R. et al. (2002). A system for stable expression of short interfering RNAs in mammalian cells. *Science* 296:550-553 (2002).

Caplan, N. J. et al. (2001). Specific inhibition of gene expression by small double-stranded RNAs in invertebrate and vertebrate systems. *Proc Natl Acad Sci USA* 98:9742-9747.

Chwen-Huey, W. et al. (2003). NELF and DSIF cause promoter proximal pausing Oil the hsp70 promoter in *Drosophila*. *Genes Dev* 17:1402-1414.

Cullen, B. R. (1986). Trans-activation of human immunodeficiency virus Occurs via a bimodal mechanism. *Cell* 46:973-982.

Dropulic, B. et al. (1996). A conditionally replicating HIV-1 vector interferes with wild-type HIV-1 replication and spread. *Proc Natl Acad Sci USA* 93:11103-11108.

Elbashir, S. M. et al. (2001). Duplexes of 21-nucleotide RNAs mediate RNA interference in cultured mammalian cells. *Nature* 411:494-498.

Feinberg, M. B. et al. (1991). The role of Tat in the human immunodeficiency virus life cycle indicates a primary effect on transcriptional elongation. *Proc Natl Acad Sci USA* 88:4045-4049.

Feng, S. and Holland, S. C. (1988). HIV-1 tat trans-activation requires the loop sequence within tar. *Nature* 334:165-167.

Fire, A. et al. (1998). Potent and specific genetic interference by double stranded RNA in *Caenorhabditis elegans*. *Nature* 391:806-811.

Fujinga, K. et al. (2004). Dynamics of Human Immunodeficiency Virus transcription: P-TEFb phosphorylates RD and dissociates negative effectors from transactivation response element. *Mol. Cell Biol.* 24:787-795.

Gasmi, M. et al. (1999). Requirements for efficient production and transduction of human immunodeficiency virus type 1-based vectors. *J Virol.* 73:1828-1834.

Graham, G. J. and Maio, J. J. (1990). RNA transcripts of the human immunodeficiency virus transactivation response element can inhibit action of the viral transactivator. *Proc Natl Acad Sci USA* 87:5817-5821.

Graham, F. and van der Eb A. (1973). A new technique for the assay of infectivity of human adenovirus 5 DNA. *Virology* 52:456-467.

Grishok, A. et al. (2001). Genes and mechanisms related to RNA interference regulate expression of the small temporal RNAs that control *C. elegans* developmental timing. *Cell* 106:23-34.

Han, P. et al. (1991). Transactivation of heterologolous promoters by HIV-1 Tat. *Nucleic Acids Res* 19:7225-7229.

Hsu, M. et al. (1996). Human fatty acid synthase gene: Evidence for the presence of two promoters and their functional interaction. *J Biol Chem* 271:13584-13592.

Hutvagner, G. et al. (2001). A cellular function for the RNA-interference enzyme Dicer in the maturation of the let-7 small temporal RNA. *Science.* 293:834-838.

Kao, S. Y. et al. (1987). Anti-termination of transcription within the long terminal repeat of HIV-1 by tat gene product. *Nature* 330:489-493.

Karn, J. (1999). Tackling Tat. *J Mol Biol* 293:235-254.

Kennerdell, J. and Carthew, R. (1998). Use of dsRNA-mediated genetic interference to demonstrate that frizzed and frizzled 2 act in the wingless pathway. *Cell* 95:1017-1026.

Kobor, M. and Greenblatt, J. (2002). Regulation of transcription elongation by phosphorylation. *Biochim Biophys Acta* 1577:261-275.

Kretz-Remy, C. and Arrigo, A. (1994). The kinetics of HIV-1 long terminal repeat transcriptional activation resemble those of hsp70 promoter in heat-shock treated HeLa cells. *FEBS Letters* 351:191-196.

Krumm, A. et al. (1993). Common mechanisms for the control of eukaryotic transcriptional elongation. *BioEssays* 15:659-665.

Lee H. et al. (1992). DNA sequence requirements for generating paused polymerase at the start of hsp70. *Genes Dev* 60:284-295.

Lee, N. S. et al. (2002). Expression of small interfering RNAs targeted against HIV-1 rev transcripts in human cells. *Nat Biotechnol* 19:500-505.

Lipardi C. et al. (2001). RNAi as randomly degraded PCR. siRNA primers convert mRNA into dsRNAs that are degraded to generate new siRNAs. *Cell* 107:297-307.

Marciniak, R. A. and Sharp, P. A. (1991). HIV-1 Tat protein promotes formation of more-processive elongation complexes. *The EMBO Journal* 10:4189-4196.

Mason, P. and Lis, J. (1997). Cooperative and competitive protein interactions at the hsp70 promoter. *J Biol Chem* 272:33227-33233.

Matsukura, S. et al. (2003). Establishment of conditional vectors for hairpin siRNA knockdowns. *Nucleic Acids Res* 31:e77.

Miyagishi, M. and Taira, K. (2002). U6 promoter-driven siRNAs with four uridine 3' overhangs efficiently suppress targeted gene expression in mammalian cells. *Nat Biotechnol* 19:457-500.

Moss, E. and Taylor, J. (2003). Small-interfering RNAs in the radar of the interferon system *Nat Cell Biol* 5:771-772.

Muesing, M. A. et al. (1987). Regulation of mRNA accumulation by a human immunodeficiency virus trans-activator protein. Cell 48:691-701.

No, D. et al. (1996). Ecdysone-inducible gene expression in mammalian cells and transgenic mice. *Proc Natl Acad Sci U S A.* 93:3346-3351.

Okamoto, T. and Wong-Staal, F. (1986). Demonstration of virus-specific transcriptional activator(s) in cells infected with HTLV-111 by an in vitro cell-free system. *Cell* 47:29-35.

Paik, S. et al. (1997). Defective HIV-1 provirus encoding a multi-target ribozyme inhibits accumulation of spliced and unspliced HIV-1 mRNAs, reduces infectivity of viral progeny, and protects the Cells from pathogenesis. *Hum Gene Ther* 8:1115-1123.

Palangat, M. et al. (1998). Transcriptional pausing at +62 of the HIV-1 nascent RNA modulates formation of the TAR RNA structure. *Mol Cell* 1:1033-1042.

Rosen, C. A. et al. (1985). The location of cis-acting regulatory sequences in the human T cell lymphotropic virus type III (HTLV-III/LAV) long terminal repeat. *Cell* 41:813 823.

Sijen, T. et al. (2001). On the role of RNA amplification in dsRNA-triggered gene silencing *Cell* 107:465-476.

Sledz, C. et al. (2003). Activation of the interferon system by short-interfering RNAs. *Nat Cell Biol* 5:834-839.

Southgate, C. and Green, M. (1991). The HIV-1 tat protein activates transcription from an upstream DNA binding site: implications for tat function. *Genes Dev* 5:2496-2507.

van de Wetering, M. et al. (2003). Specific inhibition of gene expression using a stably integrated, inducible small-interfering-RNA vector. *EMBO Rep* 4:609-615.

Wianny, F. and Zernica-Goetz, M. (2000). Specific interference with gene function by double stranded RNA in early mouse development. *Nat Cell Biol* 2:70-75.

Wiznerowicz, M. and Trono, D. (2003). Conditional suppression of cellular genes: lentivirus vector-mediated drug-inducible RNA interference. *J Virol* 77:8957-8961.

Xia, H. et al. (2002). siRNA-mediated gene silencing in vitro and in vivo. *Nat Biotechnol* 20:1006-1010.

Yi, R. et al. (2003). Exportin-5 mediates the nuclear export of pre-microRNAs and short hairpin RNAs. *Genes Dev* 17:3011-3016.

What is claimed is:

1. An inducible siRNA system for controlling expression of an siRNA molecule comprising operatively and contiguously linked in the 5' to 3' direction an inducible element, a minimal heat shock promoter, a nucleic acid sequence encoding an siRNA molecule and a minimal polyA sequence, wherein the inducible element is a viral specific transcription factor and wherein the siRNA molecule is produced only in the presence of an inducer which is specific for the inducible element.

2. The inducible siRNA system of claim 1, wherein the siRNA molecule is a short hairpin RNA (shRNA) molecule.

3. A modified cell comprising the inducible siRNA system of claim 1.

4. The inducible siRNA system of claim 1, wherein the viral specific transcription factor is an HIV TAR region, the siRNA encodes a sequence capable of inhibiting HIV replication and the inducer is HIV TAT.

5. The inducible siRNA system of claim 4, wherein the siRNA molecule is a short hairpin RNA (shRNA) molecule.

6. The modified cell of claim 3, wherein the cell is an HIV infected cell.

7. The inducible siRNA system of claim 1, wherein the minimal heat shock promoter is the *Drosophilia* hsp70 minimal heat shock promoter.

8. The inducible siRNA system of claim 1, wherein the viral specific transcription factor is an HIV TAR region.

9. The inducible siRNA system of claim 7, wherein the viral specific transcription factor is an HIV TAR region.

10. The modified cell of claim 3, wherein the viral specific transcription factor is an HIV TAR region.

11. The modified cell of claim 6, wherein the viral specific transcription factor is an HIV TAR region.

12. The inducible siRNA system of claim 1 which further comprises a cis acting regulatory element from a promoter, wherein the 3' end of the minimal polyA sequence is operatively linked and contiguous to the cis regulatory element.

13. An inducible siRNA system for controlling expression of an siRNA molecule comprising operatively and contiguously linked in the 5' to 3' direction an inducible element, a cis acting regulatory element from a promoter, a minimal heat shock promoter, a nucleic acid sequence encoding an siRNA molecule and a minimal polyA sequence, wherein the inducible element is a viral specific transcription factor and wherein the siRNA molecule is produced only in the presence of an inducer which is specific for the inducible element.

14. A modified cell comprising the inducible siRNA system of claim 7.

15. The modified cell of claim 14, wherein the viral specific transcription factor is an HIV TAR region.

16. A modified cell comprising the inducible siRNA system of claim 12.

17. The modified cell of claim 16, wherein the viral specific transcription factor is an HIV TAR region.

18. A modified cell comprising the inducible siRNA system of claim 13.

19. The modified cell of claim 18, wherein the viral specific transcription factor is an HIV TAR region.

20. A method for inhibiting viral replication in an infected cell comprising:
introducing the inducible siRNA system of claim 1 into the cell in an amount sufficient to inhibit viral replication,
wherein the nucleic acid sequence encoding the siRNA molecule encodes a sequence capable of inhibiting viral replication and wherein viral replication is inhibited in the cell.

21. The method of claim 20, wherein the siRNA molecule is a short hairpin RNA (shRNA) molecule.

22. The method of claim 20, wherein the virus is HIV, the viral specific transcription factor is the HIV TAR region and the inducer is HIV TAT.

23. A method for reducing expression of a target gene in a cell comprising:
introducing the inducible siRNA system of claim 1 into the cell in an amount sufficient to reduce expression of the target gene,
wherein the nucleic acid sequence encoding the siRNA molecule encodes a sequence that is capable of reducing expression of the target gene and wherein the expression of the target gene is reduced in the cell.

24. The method of claim 23, wherein the siRNA molecule is a short hairpin RNA (shRNA) molecule.

25. The method of claim 20, wherein the viral specific transcription factor is an HIV TAR region.

26. The method of claim 23, wherein the viral specific transcription factor is an HIV TAR region.

27. A method for inhibiting viral replication in an infected cell comprising:
introducing the inducible siRNA system of claim 12 into the cell in an amount sufficient to inhibit viral replication,
wherein the nucleic acid sequence encoding the siRNA molecule encodes a sequence capable of inhibiting viral replication and wherein viral replication is inhibited in the cell.

28. A method for inhibiting viral replication in an infected cell comprising:
introducing the inducible siRNA system of claim 13 into the cell in an amount sufficient to inhibit viral replication,
wherein the nucleic acid sequence encoding the siRNA molecule encodes a sequence capable of inhibiting viral replication and wherein viral replication is inhibited in the cell.

29. A method for reducing expression of a target gene in a cell comprising:
introducing the inducible siRNA system of claim 12 into the cell in an amount sufficient to reduce expression of the target gene,
wherein the nucleic acid sequence encoding the siRNA molecule encodes a sequence that is capable of reducing expression of the target gene and wherein target gene expression is reduced in the cell.

30. A method for reducing expression of a target gene in a cell comprising:
introducing the inducible siRNA system of claim 13 into the cell in an amount sufficient to reduce expression of the target gene,
wherein the nucleic acid sequence encoding the siRNA molecule encodes a sequence that is capable of reducing expression of the target gene and wherein target gene expression is reduced in the cell.

* * * * *

UNITED STATES PATENT AND TRADEMARK OFFICE
CERTIFICATE OF CORRECTION

PATENT NO.        : 8,138,327 B2
APPLICATION NO.   : 11/283410
DATED             : March 20, 2012
INVENTOR(S)       : Hoshang Unwalla et al.

It is certified that error appears in the above-identified patent and that said Letters Patent is hereby corrected as shown below:

*In the Specification*

Col. 1, line 2: "SIRNA" should be -- siRNA --

Col. 5, line 39: "element in" should be -- element. In --

Col. 8, line 3: "veil" should be -- well --

Col. 9, line 26: "ETSF" should be -- ETSI --

Col. 9, line 29: "tumor-suppressor" should be -- tumor suppressor --

Col. 9, line 39: "inulnases," should be -- inulinases, --

Col. 9, line 58: "Such as" should be -- such as --

Col. 12, line 9: "Such a" should be -- such a --

Col. 18, line 66: "in an" should be -- In an --

Col. 19, line 11: "Fujinga" should be -- Fujinaga --

Col. 19, line 16: "Fujinga" should be -- Fujinaga --

Col. 20, line 59: "-65" should be -- ~65 --

Col. 20, line 61: "hail-pill" should be -- hairpin --

Col. 21, line 29: "Hall" should be -- Han --

Col. 22, line 10: "oil" should be -- on --

Col. 23, line 18: "Oil" should be -- on --

Col. 23, line 38: "Fujinga" should be -- Fujinaga --

Col. 23, line 56: "heterologolous" should be -- heterologous --

Col. 24, line 48: "HTLV-111" should be -- HTLV-III --

Signed and Sealed this
Eighth Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,138,327 B2
APPLICATION NO. : 11/283410
DATED : March 20, 2012
INVENTOR(S) : Hoshang Unwalla et al.

It is certified that error appears in the above-identified patent and that said Letters Patent is hereby corrected as shown below:

In the Specification

Column 1, Lines 15-18:
"The present invention was made in part with Government support under Grant Numbers AI29329, AI42552 and HL074704 awarded by the National Institutes of Health. The Government may have certain rights in this invention."
Should be:
-- This invention was made with government support under HL074704, AI029329, and AI042552 awarded by the National Institutes of Health. The government has certain rights in the invention. --

Signed and Sealed this
Second Day of April, 2024

Katherine Kelly Vidal
Director of the United States Patent and Trademark Office